United States Patent
Filpula et al.

(10) Patent No.: US 8,071,741 B2
(45) Date of Patent: Dec. 6, 2011

(54) STABLE RECOMBINANT ADENOSINE DEAMINASE

(75) Inventors: David R. Filpula, Piscataway, NJ (US); Stephen K. Youngster, Piscataway, NJ (US)

(73) Assignee: Defiante Farmaceutica, S.A., Funchal-Madeira (PT)

( * ) Notice: Subject to any disclaimer, the term of this patent is extended or adjusted under 35 U.S.C. 154(b) by 411 days.

(21) Appl. No.: 12/105,913

(22) Filed: Apr. 18, 2008

(65) Prior Publication Data

US 2009/0047271 A1   Feb. 19, 2009

Related U.S. Application Data

(60) Provisional application No. 60/913,009, filed on Apr. 20, 2007.

(51) Int. Cl.
| C07H 21/04 | (2006.01) |
| C12P 21/02 | (2006.01) |
| C12N 9/78 | (2006.01) |
| A61K 38/50 | (2006.01) |

(52) U.S. Cl. ........ 536/23.2; 435/69.1; 435/227; 514/1.4
(58) Field of Classification Search ................. 536/23.2; 435/69.1, 227; 514/1.4
See application file for complete search history.

(56) References Cited

U.S. PATENT DOCUMENTS

| | | |
|---|---|---|
| 5,122,614 A | 6/1992 | Zalipsky |
| 5,324,844 A | 6/1994 | Zalipsky |
| 5,346,823 A | 9/1994 | Estell et al. |
| 5,349,001 A | 9/1994 | Greenwald et al. |
| 5,405,877 A | 4/1995 | Greenwald et al. |
| 5,567,422 A | 10/1996 | Greenwald |
| 5,612,460 A | 3/1997 | Zalipsky |
| 5,643,575 A | 7/1997 | Martinez et al. |
| 5,650,234 A | 7/1997 | Dolence et al. |
| 5,681,567 A | 10/1997 | Martinez et al. |
| 5,728,560 A | 3/1998 | Shorr et al. |
| 5,756,593 A | 5/1998 | Martinez et al. |
| 5,808,096 A | 9/1998 | Zalipsky |
| 5,849,549 A | 12/1998 | Barnett et al. |
| 5,919,455 A | 7/1999 | Greenwald et al. |
| 5,965,119 A | 10/1999 | Greenwald et al. |
| 6,113,906 A | 9/2000 | Greenwald et al. |
| 6,153,655 A | 11/2000 | Martinez et al. |
| 6,180,095 B1 | 1/2001 | Greenwald et al. |
| 6,207,876 B1 | 3/2001 | Kellems et al. |
| 6,251,382 B1 | 6/2001 | Greenwald et al. |
| 6,303,569 B1 | 10/2001 | Greenwald et al. |
| 6,366,860 B1 | 4/2002 | Rozzell, Jr. et al. |
| 6,395,266 B1 | 5/2002 | Martinez et al. |
| 6,556,506 B2 | 4/2003 | Naven |
| 6,624,142 B2 | 9/2003 | Zhao et al. |
| 6,638,499 B2 | 10/2003 | Martinez et al. |
| 6,703,381 B1 | 3/2004 | Ekwuribe et al. |
| 6,720,306 B2 | 4/2004 | Greenwald et al. |
| 6,824,766 B2 | 11/2004 | Greenwald et al. |
| 6,828,401 B2 | 12/2004 | Nho et al. |
| 7,053,150 B2 | 5/2006 | Kozlowski et al. |
| 7,087,229 B2 | 8/2006 | Zhao et al. |
| 7,122,189 B2 | 10/2006 | Zhao et al. |
| 7,413,738 B2 | 8/2008 | Zhao et al. |
| 2003/0215436 A1 | 11/2003 | Walsh et al. |
| 2004/0136952 A1 | 7/2004 | Bhaskaran et al. |
| 2005/0220799 A1 | 10/2005 | Sitkovsky et al. |
| 2006/0286065 A1 | 12/2006 | Zhao et al. |
| 2007/0078219 A1 | 4/2007 | Zhao et al. |
| 2007/0166276 A1 | 7/2007 | Zhao et al. |
| 2007/0173615 A1 | 7/2007 | Zhao et al. |
| 2008/0159964 A1* | 7/2008 | Blackburn et al. .............. 424/45 |
| 2008/0249260 A1 | 10/2008 | Zhao et al. |

FOREIGN PATENT DOCUMENTS

| WO | WO 2007/149686 A2 | 12/2007 |
| WO | WO 2008/034119 A2 | 3/2008 |
| WO | WO 2008/034124 A2 | 3/2008 |

OTHER PUBLICATIONS

Alignment of instant SEQ ID No. 2 with SEQ ID No. 6 of Blackburn et al., US 2008/0159964 A1, NCBI Blast 2 web site, http://blast.ncbi.nlm.nih.gov/Blast.cgi, performed on Mar. 23, 2010.*
Result 1, Geneseq protein database search, alignment of instant SEQ ID No. 1 with SEQ ID No. 5 of Blackburn et al., US 2008/0159964 A1, performed on Mar. 18, 2010.*
GenBank/NCBI, conserved domain search for instant SEQ IQ No. 1, NCBI Blast website, http://blast.ncbi.nlm.nih.gov/Blast.cgi, performed on Jul. 9, 2010.*
International Search Report and Written Opinion issued in PCT/US08160805 and dated Aug. 19, 2008.
Bota, et al. Purification of human adenosine deaminase for the preparation of a reference material. J Chromatogr B Biomed Sci Appl., 2000, vol. 737: 237-44, Abstract only.
Bhaumik et al. Mutational analysis of active site residues of human adenosine deaminase. J Biol Chem., 1993, 268: 5464-70.
Arredondo-Vega et al. Seven Novel Mutations in the Adenosine Deaminase (ADA) Gene in Patients with Severe and Delayed Onset Combined Immunodeficiency: G74C, V129M, G140E, R149W, Q199P, 462deIG and E337del. Hum Mutat., 1998, vol. 11: 482.
Lim et al. Long-term expression of human adenosine deaminase in mice transplanted with retrovirus-infected hematopoietic stem cells. Proc Natl Acad Sci USA, 1989, vol. 86: 8892-6.
Onodera et al. Successful Peripheral T-Lymphocyte-Directed Gene Transfer for a Patient With Severe Combined Immune Deficiency Caused by Adenosine Deaminase Deficiency. Blood, 1998, 91:30-6.
U.S. Appl. No. 12/105,682 Entitled: Enzymatic Anticancer Therapy, US 2009/0047270 A1.
Kinoshita et al., 2005, Biochemistry, 44:10562-10569.
Liu et al., Nat. Methods, 2007 4(3):239-44.
Xie et al., Nat. Rev. Mol. Cell. Biol., 2006 7(10):775-82.
Ryu et al., Nat. Methods, 2006 3(4):263-65.
Deiters et al., Bioorg. Med. Chem. Lett., 2004 14(23):5743-5745.
Bogosian et al., J. Biol. Chem., 1989 264(1):531-539.

(Continued)

*Primary Examiner* — Rosanne Kosson
(74) *Attorney, Agent, or Firm* — Lucas & Mercanti, LLP

(57) ABSTRACT

A mutein recombinant adenosine deaminase having any oxidizable cysteine residue replaced by a non-oxidizable amino acid residue is disclosed. Stabilized recombinant adenosine deaminase, polymer conjugates and methods of treatment using the same are also disclosed.

19 Claims, No Drawings

OTHER PUBLICATIONS

Tang et al., Biochemistry, 2002 41(34):10635-10645.
Budisa et al., Eur. J. Biochem., 1995 230(2):788-796.
Randhawa et al., Biochemistry, 1994 33(14):4352-4362.
Shearwater Corporation's 2001 catalog "Polyethylene Glycol and Derivatives for Biomedical Application".
NOF Corp. Drug Delivery System catalog, Ver. 8, Apr. 2006.
Weihofen et al., J Biol Chem, 2004 279: 43330-43335.
Ludwig et al., BBRC, 2004 313:223-229.
Weihofen et al., J Biol Chem, 2005 14911-14917.
Blay et al, Cancer Res 1997, 57: 2602-2605.
Mujoomdar et al., Biochem Pharmacol 2003, 66: 1737-1747.
Spychala, Pharmacology & Therapeutics 2000, 87:161-173.
Adair, Am J Physiol Regul Integr Comp Physiol 2005, 289: R283-396.
Sitkovsky et al., Nat Rev Immunol 2005, 5:712-721.
Merighi et al., Neoplasia 2005, 7: 894-903.
Sideraki et al. Biochemistry, 1996 35:7862-7872.

* cited by examiner

SEQUENCE LISTING

<160> NUMBER OF SEQ ID NOS: 5

<210> SEQ ID NO 1
<211> LENGTH: 356
<212> TYPE: PRT
<213> ORGANISM: Bovine
<220> FEATURE:
<221> NAME/KEY: misc_feature
<222> LOCATION: (74)..(74)
<223> OTHER INFORMATION: Cys to Ser mutein

<400> SEQUENCE: 1

```
Ala Gln Thr Pro Ala Phe Asn Lys Pro Lys Val Glu Leu His Val His
1               5                   10                  15

Leu Asp Gly Ala Ile Lys Pro Glu Thr Ile Leu Tyr Tyr Gly Arg Lys
            20                  25                  30

Arg Gly Ile Ala Leu Pro Ala Asp Thr Pro Glu Glu Leu Gln Asn Ile
        35                  40                  45

Ile Gly Met Asp Lys Pro Leu Ser Leu Pro Glu Phe Leu Ala Lys Phe
    50                  55                  60

Asp Tyr Tyr Met Pro Ala Ile Ala Gly Ser Arg Glu Ala Val Lys Arg
65                  70                  75                  80

Ile Ala Tyr Glu Phe Val Glu Met Lys Ala Lys Asp Gly Val Val Tyr
                85                  90                  95

Val Glu Val Arg Tyr Ser Pro His Leu Leu Ala Asn Ser Lys Val Glu
            100                 105                 110

Pro Ile Pro Trp Asn Gln Ala Glu Gly Asp Leu Thr Pro Asp Glu Val
        115                 120                 125

Val Ser Leu Val Asn Gln Gly Leu Gln Glu Gly Glu Arg Asp Phe Gly
    130                 135                 140

Val Lys Val Arg Ser Ile Leu Cys Cys Met Arg His Gln Pro Ser Trp
145                 150                 155                 160

Ser Ser Glu Val Val Glu Leu Cys Lys Lys Tyr Arg Glu Gln Thr Val
                165                 170                 175

Val Ala Ile Asp Leu Ala Gly Asp Glu Thr Ile Glu Gly Ser Ser Leu
            180                 185                 190

Phe Pro Gly His Val Lys Ala Tyr Ala Glu Ala Val Lys Ser Gly Val
        195                 200                 205

His Arg Thr Val His Ala Gly Glu Val Gly Ser Ala Asn Val Val Lys
    210                 215                 220

Glu Ala Val Asp Thr Leu Lys Thr Glu Arg Leu Gly His Gly Tyr His
225                 230                 235                 240

Thr Leu Glu Asp Thr Thr Leu Tyr Asn Arg Leu Arg Gln Glu Asn Met
                245                 250                 255

His Phe Glu Val Cys Pro Trp Ser Ser Tyr Leu Thr Gly Ala Trp Lys
            260                 265                 270

Pro Asp Thr Glu His Pro Val Val Arg Phe Lys Asn Asp Gln Val Asn
        275                 280                 285

Tyr Ser Leu Asn Thr Asp Asp Pro Leu Ile Phe Lys Ser Thr Leu Asp
    290                 295                 300

Thr Asp Tyr Gln Met Thr Lys Asn Glu Met Gly Phe Thr Glu Glu Glu
305                 310                 315                 320

Phe Lys Arg Leu Asn Ile Asn Ala Ala Lys Ser Ser Phe Leu Pro Glu
                325                 330                 335

Asp Glu Lys Lys Glu Leu Leu Asp Leu Leu Tyr Lys Ala Tyr Gly Met
```

```
                340           345           350
Pro Ser Pro Ala
        355

<210> SEQ ID NO 2
<211> LENGTH: 1074
<212> TYPE: DNA
<213> ORGANISM: Bovine

<400> SEQUENCE: 2
atggctcaga ccccggcttt caacaaaccg aaggtagaac tgcacgtaca cctggatggt      60
gctatcaaac cggagactat cctgtactat ggtcgtaagc gtggcatcgc tctgccggct     120
gacactccgg aagaactgca gaacatcatc ggcatggaca aaccgctgtc tctgccggaa     180
ttcctggcta aattcgacta ctacatgccg gctatcgctg gttctcgtga agcagtcaaa     240
cgtatcgctt acgaattcgt agaaatgaaa gctaaagatg gtgtagtata cgttgaagtt     300
cgttactctc cgcacctgct ggcaaactct aaagttgaac cgatcccgtg aaccaggca      360
gaaggcgatc tgactccgga tgaagtagtt tctctggtta ccagggtct gcaggagggt      420
gaacgcgatt tcggcgtaaa agttcgttct atcctgtgct gcatgcgcca ccagccgtct     480
tggtcttctg aagttgttga actgtgcaag aaataccgtg agcagaccgt agttgctatc     540
gatctggcag gtgatgaaac catcgaaggt tcttctctgt tccgggtca cgtaaaggct      600
tatgctgaag ctgttaaatc tggcgtacac cgtactgtac acgcaggtga agttggttct     660
gctaacgttg ttaaagaagc tgttgacacc ctgaaaactg aacgcctggg tcacggctac     720
cacaccctgg aagacaccac cctgtacaac cgtctgcgtc aggaaaacat gcacttcgaa     780
gtttgtccgt ggtcctctta cctgactggt gcttggaaac cggacaccga cacccggtt     840
gttcgtttca aaacgacca ggtaaactac tctctgaaca ctgacgatcc gctgatcttc      900
aaatctaccc tggacaccga ctaccagatg accaaaaacg aaatgggttt cactgaagaa     960
gaattcaaac gtctgaacat caacgctgct aagtcctctt ttctgccgga agatgagaaa    1020
aaagaactgc tggaccctgct gtacaaggca tacggtatgc cgtctccggc ttaa          1074

<210> SEQ ID NO 3
<211> LENGTH: 362
<212> TYPE: PRT
<213> ORGANISM: Human
<220> FEATURE:
<221> NAME/KEY: misc_feature
<222> LOCATION: (74)..(74)
<223> OTHER INFORMATION: Cys to Ser mutein

<400> SEQUENCE: 3

Ala Gln Thr Pro Ala Phe Asp Lys Pro Lys Val Glu Leu His Val His
1               5                   10                  15

Leu Asp Gly Ser Ile Lys Pro Glu Thr Ile Leu Tyr Tyr Gly Arg Arg
            20                  25                  30

Arg Gly Ile Ala Leu Pro Ala Asn Thr Ala Glu Gly Leu Leu Asn Val
        35                  40                  45

Ile Gly Met Asp Lys Pro Leu Thr Leu Pro Asp Phe Leu Ala Lys Phe
    50                  55                  60

Asp Tyr Tyr Met Pro Ala Ile Ala Gly Ser Arg Glu Ala Ile Lys Arg
65                  70                  75                  80

Ile Ala Tyr Glu Phe Val Glu Met Lys Ala Lys Glu Gly Val Val Tyr
                85                  90                  95

Val Glu Val Arg Tyr Ser Pro His Leu Leu Ala Asn Ser Lys Val Glu
```

```
                          100                 105                 110
Pro Ile Pro Trp Asn Gln Ala Glu Gly Asp Leu Thr Pro Asp Glu Val
        115                 120                 125

Val Ala Leu Val Gly Gln Gly Leu Gln Glu Gly Glu Arg Asp Phe Gly
        130                 135                 140

Val Lys Ala Arg Ser Ile Leu Cys Cys Met Arg His Gln Pro Asn Trp
145                 150                 155                 160

Ser Pro Lys Val Val Glu Leu Cys Lys Lys Tyr Gln Gln Gln Thr Val
                165                 170                 175

Val Ala Ile Asp Leu Ala Gly Asp Glu Thr Ile Pro Gly Ser Ser Leu
                180                 185                 190

Leu Pro Gly His Val Gln Ala Tyr Gln Glu Ala Val Lys Ser Gly Ile
            195                 200                 205

His Arg Thr Val His Ala Gly Glu Val Gly Ser Ala Glu Val Val Lys
        210                 215                 220

Glu Ala Val Asp Ile Leu Lys Thr Glu Arg Leu Gly His Gly Tyr His
225                 230                 235                 240

Thr Leu Glu Asp Gln Ala Leu Tyr Asn Arg Leu Arg Gln Glu Asn Met
                245                 250                 255

His Phe Glu Ile Cys Pro Trp Ser Ser Tyr Leu Thr Gly Ala Trp Lys
                260                 265                 270

Pro Asp Thr Glu His Ala Val Ile Arg Leu Lys Asn Asp Gln Ala Asn
            275                 280                 285

Tyr Ser Leu Asn Thr Asp Asp Pro Leu Ile Phe Lys Ser Thr Leu Asp
        290                 295                 300

Thr Asp Tyr Gln Met Thr Lys Arg Asp Met Gly Phe Thr Glu Glu Glu
305                 310                 315                 320

Phe Lys Arg Leu Asn Ile Asn Ala Ala Lys Ser Ser Phe Leu Pro Glu
                325                 330                 335

Asp Glu Lys Arg Glu Leu Leu Asp Leu Leu Tyr Lys Ala Tyr Gly Met
            340                 345                 350

Pro Pro Ser Ala Ser Ala Gly Gln Asn Leu
        355                 360

<210> SEQ ID NO 4
<211> LENGTH: 1089
<212> TYPE: DNA
<213> ORGANISM: Human

<400> SEQUENCE: 4
atggctcaga cacccgcatt tgataaaccg aaagtggaac tgcatgtcca cctggatggt      60
agcatcaaac cggaaactat cttatattac ggtcggcgtc gtggtattgc gttgccggca     120
aacacggctg aaggtttgct gaacgtgatc ggcatggaca aaccgctgac cttgccggat     180
tttttggcga aatttgatta ttatatgccg gcgattgctg ttcccgcga ggcaatcaaa      240
cgcatcgcgt atgagtttgt tgaaatgaaa gcgaagaag gcgttgtgta tgttgaggtc      300
cgttacagtc gcatctgct ggctaacagc aaggtagaac ctatcccctg aaccaagct       360
gaaggcgatc tgacgccgga tgaagtggtt gctctggtgg gtcagggttt acaggagggg     420
gagcgcgatt ttggcgttaa agctcgctct attttatgtt gcatgcgcca tcagcccaat     480
tggtccccga agtggttga actttgtaaa agtaccaac aacagaccgt tgtcgcgatt       540
gatttggcag gcgatgaaac aattccaggc agctccctgt tgccagggca cgtgcaagcg     600
taccaagaag cagtgaaaag cggcatccac cggactgtcc acgccggcga ggtcggtagc     660
```

```
gccgaggttg tgaaagaagc cgtggacatc ctgaaaaccg agcggctggg ccatgggtac      720
cacacactgg aggatcaggc attatataac cgcttacgcc aggaaaatat gcatttcgaa      780
atttgtccgt ggagtagtta cttaactggc gcgtggaaac cggataccga acatgcggtt      840
atccgcttaa agaatgatca agcaaattac agtctgaata cagatgatcc cctgattttc      900
aagtctaccc tggacacaga ttatcagatg acgaagcggg atatgggatt tacggaagaa      960
gaatttaagc gtctcaatat caatgcggcg aaatcttcat ttctgccgga agatgagaaa     1020
cgtgagttgc tggatcttct gtacaaggcc tacggtatgc cgccgagcgc atcggccggg     1080
cagaacctg                                                             1089

<210> SEQ ID NO 5
<211> LENGTH: 356
<212> TYPE: PRT
<213> ORGANISM: Bovine

<400> SEQUENCE: 5
```

Ala Gln Thr Pro Ala Phe Asn Lys Pro Lys Val Glu Leu His Val His
1               5                   10                  15

Leu Asp Gly Ala Ile Lys Pro Glu Thr Ile Leu Tyr Tyr Gly Arg Lys
            20                  25                  30

Arg Gly Ile Ala Leu Pro Ala Asp Thr Pro Glu Glu Leu Gln Asn Ile
        35                  40                  45

Ile Gly Met Asp Lys Pro Leu Ser Leu Pro Glu Phe Leu Ala Lys Phe
    50                  55                  60

Asp Tyr Tyr Met Pro Ala Ile Ala Gly Cys Arg Glu Ala Val Lys Arg
65                  70                  75                  80

Ile Ala Tyr Glu Phe Val Glu Met Lys Ala Lys Asp Gly Val Val Tyr
                85                  90                  95

Val Glu Val Arg Tyr Ser Pro His Leu Leu Ala Asn Ser Lys Val Glu
            100                 105                 110

Pro Ile Pro Trp Asn Gln Ala Glu Gly Asp Leu Thr Pro Asp Glu Val
        115                 120                 125

Val Ser Leu Val Asn Gln Gly Leu Gln Glu Gly Glu Arg Asp Phe Gly
    130                 135                 140

Val Lys Val Arg Ser Ile Leu Cys Cys Met Arg His Gln Pro Ser Trp
145                 150                 155                 160

Ser Ser Glu Val Val Glu Leu Cys Lys Lys Tyr Arg Glu Gln Thr Val
                165                 170                 175

Val Ala Ile Asp Leu Ala Gly Asp Glu Thr Ile Glu Gly Ser Ser Leu
            180                 185                 190

Phe Pro Gly His Val Lys Ala Tyr Ala Glu Ala Val Lys Ser Gly Val
        195                 200                 205

His Arg Thr Val His Ala Gly Glu Val Gly Ser Ala Asn Val Val Lys
    210                 215                 220

Glu Ala Val Asp Thr Leu Lys Thr Glu Arg Leu Gly His Gly Tyr His
225                 230                 235                 240

Thr Leu Glu Asp Thr Thr Leu Tyr Asn Arg Leu Arg Gln Glu Asn Met
                245                 250                 255

His Phe Glu Val Cys Pro Trp Ser Ser Tyr Leu Thr Gly Ala Trp Lys
            260                 265                 270

Pro Asp Thr Glu His Pro Val Val Arg Phe Lys Asn Asp Gln Val Asn
        275                 280                 285

Tyr Ser Leu Asn Thr Asp Asp Pro Leu Ile Phe Lys Ser Thr Leu Asp
    290                 295                 300

```
Thr Asp Tyr Gln Met Thr Lys Asn Glu Met Gly Phe Thr Glu Glu Glu
305                 310                 315                 320

Phe Lys Arg Leu Asn Ile Asn Ala Ala Lys Ser Ser Phe Leu Pro Glu
                325                 330                 335

Asp Glu Lys Lys Glu Leu Leu Asp Leu Leu Tyr Lys Ala Tyr Gly Met
            340                 345                 350

Pro Ser Pro Ala
        355
```

STABLE RECOMBINANT ADENOSINE DEAMINASE

CROSS-REFERENCE TO RELATED APPLICATION

This application claims the benefit of priority from U.S. Provisional Patent Application Ser. Nos. 60/913,009 filed Apr. 20, 2007, the contents of which are incorporated herein by reference.

FIELD OF THE INVENTION

The invention provides recombinant adenosine deaminase mutated for enhanced stability.

BACKGROUND OF THE INVENTION

Adenosine deaminase (ADA) has been used in the treatment of an enzyme deficiency disorder called severe combined immunodeficiency disease (SCID) or "Bubble boy" disease for some time. For more than 15 years, Enzon Pharmaceuticals has made therapeutic ADA available for patients in the form of a PEGylated ADA prepared using a bovine source of the ADA enzyme.

Recently, there have been efforts to replace the bovine source enzyme with a recombinant source enzyme (hereinafter "rADA"). Both recombinant human ("rhADA") and recombinant bovine ("rbADA") have been considered as replacements for purified natural bovine ADA. The rbADA and rhADA enzymes are somewhat less stable than the native purified bovine enzyme that is currently employed. Both rhADA and rbADA are believed to degrade in a manner consistent with cysteine degradation: addition of oxygen; formation of dithiols; increasing degradation as pH increases; precipitation, especially as the pH is increased and the samples are concentrated. In the reduced state, cysteine contains a reactive —SH group (sulfhydryl) which is the form responsible for die degradation.

Evidence has suggested that a single, exposed cysteine may be responsible for the degradation that is seen for both rbADA and rhADA. Bovine ADA (i.e., native bovine ADA purified from bovine source) has a structure very similar to that of rhADA: both bovine ADA and rhADA have the same number of cysteines in the same positions of the primary sequence. Currently obtained recombinant human and recombinant bovine ADA contain degradants/impurities (dithiols) that are consistent with cysteine reactivity. Native bovine ADA differs structurally from recombinant bovine ADA in that native bovine ADA has a single mole of cysteine bound to each mole of ADA. Native bovine ADA is also stable to high pH, suggesting that the cysteine bound to the ADA is functioning as a protecting group.

One method for stabilizing recombinant human and/or recombinant bovine ADA is to cap the active Cys residue (Cys 74 of both mature rbADA and mature rhADA) with any one of oxidized glutathione, iodoacetamide, iodoacetic acid, cystine, other dithiols and mixtures thereof. This method is set forth by co-owned U.S. patent application Ser. No. 11/738,012, entitled, "Stabilized Proteins", the contents of which are incorporated by reference herein in their entirety.

Despite the foregoing, it would be advantageous to avoid the need for an additional capping step by modifying the protein structure to provide inherent stability immediately upon expression. U.S. Pat. No. 5,346,823 describes the stabilization of prokaryotic proteases such as subtilisin, and neutral protease, by replacing destabilizing Cys residues with Ser and other amino acid residues, by mutation. However, mutational analysis of active sites in ADA revealed that replacement of a Cys residue (Cys 262) resulted in an enzyme with significantly decreased activity, Bhaumik et al. 1993, *The J. of Biol Chem,* 268. (8):5464-5470. Thus, before the present invention, it was not known to stabilize adenosine deaminase enzymes by replacing an active and exposed Cys residue by another amino acid residue while retaining optimal useful enzyme activity.

Thus, it would be beneficial to provide both rbADA and rhADA that is stable, i.e., without significant degradation during storage and processing, at pH levels which are useful for optimum PEGylation of the enzyme.

SUMMARY OF THE INVENTION

Accordingly, the invention provides for a recombinant ADA having any oxidizable cysteine residue replaced by a non-oxidizable amino acid residue, relative to the wild-type form of the ADA enzyme. The mutein ADA includes a non-oxidizable amino acid residue that is one of the naturally-occurring L-amino acids, e.g., alanine, aspartic acid, glutamic acid, phenylalanine, glycine, histidine, isoleucine, lysine, leucine, methionine, asparagine, proline, glutamine, arginine, serine, threonine, valine, tryptophan, tyrosine and/or art-known variations and derivatives of the naturally occurring L-amino acids, e.g., 2-aminoadipic acid, 3-aminoadipic acid, beta-alanine, beta-aminopropionic acid, 2-aminobutyric acid, 4-amino/butyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methylvaline, norvaline, norleucine and ornithine, and the like. Optionally, methionine or tryptophan are avoided as these are potentially oxidizable.

More preferably, the non-oxidizable amino acid residue is one of serine, alanine, asparagine, glutamine, glycine, isoleucine, leucine, phenylalanine, threonine, tyrosine, and valine. Serine is most preferred. In certain preferred embodiments, the oxidizable cysteine is located at about position 74 of the mature ADA protein. The recombinant ADA is preferably a recombinant bovine ADA or a recombinant human ADA that is, e.g., translated from a DNA molecule according to SEQ ID NO: 2 or SEQ ID NO: 4 and that preferably comprises SEQ ID NO: 1 or SEQ ID NO: 3. When the recombinant ADA is a recombinant bovine ADA according to SEQ ID NO: 1, the ADA optionally is expressed with a polymorphism selected from one or more of Gln in place of $Lys_{198}$; Ala in place of $Thr_{245}$; and Arg in place of $Gly_{351}$.

The invention also provides a polyalkylene oxide-ADA conjugate, wherein the polyalkylene oxide is preferably a polyethylene glycol. Optionally, the polyethylene glycol is conjugated to the recombinant adenosine deaminase via a linker chemistry selected from the group consisting of succinimidyl carbonate, thiazolidine thione, urethane, succinimidyl succinate, and amide based linkers. The succinimidyl carbonate is preferred. The polyethylene glycol is preferably covalently attached to an epsilon amino group of a Lys of the recombinant adenosine deaminase.

The polyethylene glycol-ADA conjugate comprises at least 1 (i.e., one or more) polyethylene glycol strands attached to epsilon amino groups, preferably at least 5 (i.e., five or more) polyethylene glycol strands attached to epsilon amino groups, or more preferably, from about 11 to about 18 polyethylene glycol strands attached to epsilon amino groups, of Lys residues of the recombinant ADA.

The polyethylene glycol of the inventive conjugates has a molecular weight of from about 2,000 to about 100,000 kDa, or more preferably from about 4,000 to about 45,000 kDa.

The invention further provides a process for purifying the recombinant adenosine deaminases of the invention. For example, the recombinant adenosine deaminase is preferably purified by ion exchange chromatography (e.g., Capto Q, DEAE and SP chromatography), and the recombinant adenosine deaminase of SEQ ID NO: 1, is preferably purified by hydrophobic interaction chromatography.

The invention still further provides a method of treating an ADA-mediated condition in mammals, comprising administering an effective amount of the inventive recombinant ADA. The ADA-mediated condition includes, e.g., SCID, cancer, and the like.

DETAILED DESCRIPTION OF THE INVENTION

Stable recombinant adenosine deaminase enzymes are provided herein. The inventive adenosine deaminase enzymes are provided by replacing a cysteine residue that is subject to oxidation processes when the enzyme is in solution, with an acceptable alternative amino acid residue that conserves the activity, charge and tertiary structure of the enzyme while removing a source of breakdown instability.

A. DEFINITIONS

In order to provide a clear description of the invention, several terms are defined, as follows.

The term, "recombinant" refers to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous (exogenous or foreign) nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, under-expressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

The term, "encoding" with respect to a specified nucleic acid, includes reference to nucleic acids which comprise the information for translation into the specified protein. The information is specified by the use of codons.

A "host cell" is a cell which can support the replication or expression of the expression vector. Host cells may be prokaryotic cells such as E. coli, or eukaryotic cells such as yeast, insect, amphibian, or mammalian cells.

As used herein, "polypeptide", "peptide" and "protein" are used interchangeably and include reference to a polymer of amino acid residues.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

"Transfection" refers to the taking up of an expression vector by a host cell, whether or not any coding sequences are in fact expressed. Numerous methods of transfection are known to the ordinarily skilled artisan. For example, transfection is accomplished in the presence of an expression vector and high concentrations of $CaPO_4$, by electroporation, by use of a phage or viral expression vector for insertion into a host cell, by mechanical insertion of nucleic acid, and even by culturing the host cells in the presence of unpackaged nucleic acid fragments. Successful transfection is generally recognized when any indication of the operation of the vector of interest occurs within the host cell.

"Transformation" describes the introduction of a nucleic acid into an organism so that the nucleic acid is replicable, either as an extrachromosomal element or by integration in the host chromosome. Depending on the host cell used, transformation is accomplished using art known methods appropriate to particular host cells. The calcium treatment employing calcium chloride, as described by Cohen, S, N. *Proc. Natl. Acad. Sci.* (USA), 69: 2110 (1972) and Mandel et al., *J. Mol. Biol.* 53:154 (1970), is generally used for prokaryotes or other cells that are encapsulated within cellular walls (e.g., many bacterial and/or plant cells). For mammalian cells without such cell walls, the calcium phosphate precipitation method of Graham, F. and van der Eb, A., *Virology*, 52: 456-457 (1978) is preferred. General aspects of mammalian cell host system transformations have been described in U.S. Pat. No. 4,399,216 issued Aug. 16, 1983. Transformations into yeast are typically carried out according to the method of Van Solingen. P., et al., *J. Bact.*, 130: 946 (1977) and Hsiao, C. L., et al., *Proc. Natl. Acad. Sci.* (USA) 76: 3829 (1979). However, any other art-known methods for introducing nucleic acid, e.g., DNA, into cells, such as, for example, by nuclear injection, lipofection, or by protoplast fusion, may also be used.

As used herein, the term "complementary" with respect to a nucleic acid refers to the opposite strand (using Watson-Crick base pairing) produced when a first nucleic acid molecule is replicated using that molecule as a template, to form a new, second nucleic acid strand. In one aspect of the invention, two nucleic acid molecules are considered to be complementary, each to the other, when they hybridize or bind together under stringent conditions.

"Operably linked" refers to a juxtaposition of components, e.g., a regulatory region and an open reading frame, such that the normal function of the components can be performed. Thus, an open reading frame that is "operably linked" to control sequences refers to a configuration wherein die coding sequence can be expressed under the control of these sequences.

"Control Sequences" refers to nucleic acid sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize, for example, such control sequences as promoters, polyadenylation signals, and enhancers, to name but a few.

"Expression system" or "expression vector" refers to nucleic acid sequences containing a desired coding sequence and control sequences in operable linkage, so that hosts transformed with these sequences are capable of producing the encoded proteins. To effect transformation, the expression system may be included on a vector; however, the relevant nucleic acid molecule may then also be integrated into the host chromosome.

As used herein, "cell," "cell line," and "cell culture" are used interchangeably and all such designations include progeny. Thus, "transformants" or "transformed cells" include the primary subject cell and cultures derived therefrom without regard for the number of transfers. It is also understood that all progeny may not be precisely identical in genomic content, due to deliberate or inadvertent mutations. Mutant progeny that have the same functionality as screened for in the originally transformed cell are included. Where distinct designations are intended, it will be clear from the context.

For purposes of the present invention, the term "residue" shall be understood to mean that portion of a compound, to which it refers, e.g., PEG, ADA, amino acid, etc. that remains after it has undergone a substitution reaction with another compound.

For purposes of the present invention, the term "polymeric residue" e.g., "PEG residue" shall each be understood to mean that portion of the polymer or PEG which remains after it has undergone a reaction with other compounds, moieties, etc.

For purposes of the present invention, the term "alkyl" as used herein refers to a saturated aliphatic hydrocarbon, including straight-chain, branched-chain, and cyclic alkyl groups. The term "alkyl" also includes alkyl-thio-alkyl, alkoxyalkyl, cycloalkylalkyl, heterocycloalkyl, and $C_{1-6}$ alkylcarbonylalkyl groups. Preferably, the alkyl group has 1 to 12 carbons. More preferably, it is a lower alkyl of from about 1 to 7 carbons, yet more preferably about 1 to 4 carbons. The alkyl group can be substituted or unsubstituted. When substituted, the substituted group(s) preferably include halo, oxy, azido, nitro, cyano, alkyl, alkoxy, alkyl-thio, alkyl-thio-alkyl, alkoxyalkyl, alkyl amino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ hydrocarbonyl, aryl, and amino groups.

For purposes of the present invention, the term "substituted" as used herein refers to adding or replacing one or more atoms contained within a functional group or compound with one of the moieties from the group of halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ carbonyl, aryl, and amino groups.

The term "alkenyl" as used herein refers to groups containing at least one carbon-carbon double bond, including straight-chain, branched-chain, and cyclic groups. Preferably, the alkenyl group has about 2 to 12 carbons. More preferably, it is a lower alkenyl of from about 2 to 7 carbons, yet more preferably about 2 to 4 carbons. The alkenyl group can be substituted or unsubstituted. When substituted the substituted group(s) preferably include halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ alkylcarbonylalkyl, aryl, and amino groups.

The term "alkynyl" as used herein refers to groups containing at least one carbon-carbon triple bond, including straight-chain, branched-chain, and cyclic groups. Preferably, the alkynyl group has about 2 to 12 carbons. More preferably, it is a lower alkynyl of from about 2 to 7 carbons, yet more preferably about 2 to 4 carbons. The alkynyl group can be substituted or unsubstituted. When substituted the substituted group(s) preferably include halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ hydrocarbonyl, aryl, and amino groups. Examples of "alkynyl" include propargyl, propyne, and 3-hexyne.

For purposes of the present invention, the term "aryl" refers to an aromatic hydrocarbon ring system containing at least one aromatic ring. The aromatic ring can optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

For purposes of the present invention, the term "cycloalkyl" refers to a $C_{3-8}$ cyclic hydrocarbon. Examples of cycloalkyl include cyclopropyl, cyclobutyl, cyclopentyl, cyclohexyl, cycloheptyl and cyclooctyl.

For purposes of the present invention, the term "cycloalkenyl" refers to a $C_{3-8}$ cyclic hydrocarbon containing at least one carbon-carbon double bond. Examples of cycloalkenyl include cyclopentenyl, cyclopentadienyl, cyclohexenyl, 1,3-cyclohexadienyl, cycloheptenyl, cycloheptatrienyl, and cyclooctenyl.

For purposes of the present invention, the term "cycloalkylalkyl" refers to an alklyl group substituted with a $C_{3-9}$ cycloalkyl group. Examples of cycloalkylalkyl groups include cyclopropyl methyl and cyclopentyl ethyl.

For purposes of the present invention, the term "alkoxy" refers to an alkyl group of indicated number of carbon atoms attached to the parent molecular moiety through an oxygen bridge. Examples of alkoxy groups include, for example, methoxy, ethoxy, propoxy and isopropoxy.

For purposes of the present invention, an "alkylaryl" group refers to an aryl group substituted with an alkyl group.

For purposes of the present invention, an "aralkyl" group refers to an alkyl group substituted with an aryl group.

For purposes of the present invention, the term "alkoxyalkyl" group refers to an alkyl group substituted with an alkloxy group.

For purposes of the present invention, the term "alkyl-thio-alkyl" refers to an alkyl-S-alkyl thioether, for example methylthiomethyl or methylthioethyl.

For purposes of the present invention, the term "amino" refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

For purposes of the present invention, the term "alkylcarbonyl" refers to a carbonyl group substituted with alkyl group.

For purposes of the present invention, the terms "halogen" or "halo" refer to fluorine, chlorine, bromine, and iodine.

For purposes of the present invention, the term "heterocycloalkyl" refers to a non-aromatic ring system containing at least one heteroatom selected from nitrogen, oxygen, and sulfur. The heterocycloalkyl ring can be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrrolidinyl.

For purposes of the present invention, the term "heteroaryl" refers to an aromatic rind system containing at least one heteroatom selected from nitrogen, oxygen, and sulfur. The heteroaryl ring can be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

For purposes of the present invention, the term "heteroatom" refers to nitrogen, oxygen, and sulfur.

In some embodiments, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkyniyls and mercaptoalkynyls; substituted cycloalkyls include moieties such as 4-chlorocyclohexyl; aryls include moieties such as napthyl; substituted aryls include moieties such as 3-bromo phenyl; aralkyls include moieties such as tolyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo shall be understood to include fluoro, chloro, iodo and bromo.

For purposes of the present invention, "positive integer-" shall be understood to include an integer equal to or greater than 1 and as will be understood by those of ordinary skill to be within the realm of reasonableness by the artisan of ordinary skill.

For purposes of the present invention, the term "linked" shall be understood to include covalent (preferably) or non-covalent attachment of one group to another, i.e., as a result of a chemical reaction.

The terms "effective amounts" and "sufficient amounts" for purposes of the present invention shall mean an amount which achieves a desired effect or therapeutic effect as such effect is understood by those of ordinary skill in the art.

For purposes of the present invention, the term "adenosine" shall be understood to include the nucleosides adenosine and deoxyadenosine. Adenosine also includes adenosine and deoxyadenosine present in the form of AMP, ADP, ATP, dAMP, dADP or dATP.

For purposes of the present invention, "adenosine-mediated condition" or "adenosine deaminase-responsive condition" shall be understood as broadly including any diseases, conditions or disorders which benefit from the administration of ADA, or active fraction thereof, etc., regardless of the route of administration.

For purposes of the present invention, "treatment of an adenosine-mediated condition" or "treatment of an adenosine deaminase-responsive condition" such as SCID shall be understood to mean that symptoms or conditions are avoided, minimized or attenuated when compared to that observed in the absence of the ADA treatment. The treated conditions can be confirmed by, for example, decrease in adenosine.

Broadly speaking, a successful treatment of the adenosine-mediated condition shall be deemed to occur when the desired clinical response is obtained. Alternatively, a successful treatment can be defined by obtaining at least 20% or preferably 30%, more preferably 40% or higher (i.e., 50% or 80%) decrease in adenosine, including other clinical markers contemplated by the artisan in the field, when compared to that observed in the absence of the ADA treatment.

Furthermore, the use of singular terms for convenience in description is in no way intended to be so limiting. Thus, for example, reference to a composition comprising an enzyme refers to one or more molecules of that enzyme. It is also to be understood that this invention is not limited to the particular configurations, process steps, and materials disclosed herein as such configurations, process steps, and materials may vary somewhat.

It is also to be understood that the terminology employed herein is used for the purpose of describing particular embodiments only and is not intended to be limiting, since the scope of the present invention will be limited by the appended claims and equivalents thereof.

B. RECOMBINANTLY PRODUCED ADA ENZYMES

Initial efforts to obtain recombinant ADA enzyme, including enzymes expressed from human or bovine derived genes, uncovered a storage instability not previously seen with natural ADA derived from bovine intestine. Studies of the breakdown products of rhADA and rbADA were conducted, and confirmed that both ADA enzymes degrade in a manner consistent with cysteine degradation. For example, the addition of oxygen to rhADA results in the formation of compounds more hydrophilic than rhADA that have masses 16 and 32 Da higher than rhADA. In addition, this results in the formation of dithiols (as indicated by reversal of a subpopulation of degradants by addition of dithiothreitol ["DTT"]; increasing, degradation as pH increases; precipitation, especially as pH is increased and samples are concentrated, suggesting intermolecular disulfide bond formation producing insoluble aggregates.

We have determined that a single, exposed cysteine is responsible for the degradation that is seen for rhADA. Bovine ADA (undegraded) has a structure very similar to that of rhADA: both bovine ADA and rhADA have the same number of cysteines in the same positions of the primary sequence. rbADA also contains degradants/impurities (dithiols) that are consistent with cysteine reactivity. Native bovine ADA differs structurally from rbADA in that it has a single mole of cysteine bound to each mole of ADA, and native bovine ADA is stable to high pH, suggesting that the cysteine bound to the ADA is functioning as a protecting group. The cysteine bound to native bovine ADA can be removed by treatment with a reducing agent, such as mercaptoethanol or DTT. While not wishing to be bound by any theory or hypothesis, this suggests that the cysteine group is conjugated to the ADA via a disulfide bond as follows:

where one cysteine in the primary sequence of ADA is bound to a molecule of cysteine. Cysteines engaged in such disulfide bonds are stable towards the oxidative degradation pathways mentioned in the first paragraph. Cysteine residues occur at positions 74, 152, 153, 168, and 261 of both human and bovine mature ADA. Inspection of the 3-dimensional structure of bovine ADA obtained by X-ray crystallography (Kinoshita et al., 2005, *Biochemistry*, 44:10562-10569) indicates that the cysteines at positions 74, 152, 1553, 168, and 261 have no opportunity for engaging in intramolecular disulfide bonds. Structural geometrical constraints are known to generally prevent vicinal cysteine residues, such as those occurring at positions 152 and 153 of ADA, from engaging in disulfide bonds. Thus, all cysteine residues are potentially in the reduced state and, consequently, are potential candidate sites for oxidative degradation reactions. However, visual inspection of the 3-dimensional structure of bovine ADA cited supra, indicates that cysteine 74 is clearly exposed to the solvent to a greater degree than are the other four cysteines and, furthermore, that the other four cysteines appear to be buried within the enzyme structure to a degree that would likely prevent significant interaction with solvated reactants (provided the protein is not denatured). The existence of a single reactive cysteine residue would explain the mono-derivatization of native bovine adenosine deaminase which presumably results from post-translational modification.

The facts above indicated that a reactive cysteine at position 74 may be responsible for the degradation seen in rhADA and rbADA and that capping the reactive —S—H group of the cysteine will protect rhADA or rbADA from the apparent oxidative degradation pathways seen for those recombinant enzymes. The following experiment was done to determine whether this was the case. Recombinant hADA, at a concentration of approximately 0.6 mg/mL, was reacted with 125 mM iodoacetamide (IAA) in sodium phosphate buffer at pH 7.4 for 16 hours at 37° C. Within several minutes of beginning the reaction, analysis of the sample by RP-HPLC with UV and mass spectrometric detection showed that approximately 70.9% of the rhADA was monoderivatized with IAA and 17.2% was derivatized at two sites. After 2 and 16 hours incubation, the chromatographic profile was not significantly changed, indicating that the derivative was stable towards the oxidative degradation pathways typical of rhADA. A similar sample of rhADA was prepared that lacked IAA and was analyzed similarly. After 16 hours incubation at 37° C. at pH 7.4, the rhADA protein degraded to an extent of 30% (beyond the degradation that the sample had initially). The results are consistent with a single, predominant exposed cysteine that can be protected by capping with iodoacetamide. These experiments are described in greater detail by co-owned U.S. patent application Ser. No. 11/738,012, entitled, "Stabilized Proteins," incorporated by reference herein, as cited supra.

While capping is effective in eliminating the oxidative degradation of the reactive cysteine in ADA, employment of such a capped enzyme requires an added manufacturing step. Thus, direct elimination of the unstable Cys residue from the encoding gene by substitution with a different amino acid, was investigated. A suitable replacement amino acid is one that is not subject to the same type of oxidation, will not disrupt the tertiary structure of the folded ADA protein, and in the typical embodiment of the invention is selected so as not to undergo random conjugation to activated polyalkylene oxide during conjugate formation. Any of the art-known naturally occurring amino acids and/or non-naturally occurring amino acids and/or derivatives thereof that meet this criteria are contemplated to be suitable for replacing an oxidizable cysteine according to the invention. An exemplary list of such amino acids includes naturally-occurring L-amino acids such as: alanine, aspartic acid, glutamic acid, phenylalanine, glycine, histidine, isoleucine, lysine, leucine, methionine, asparagine, proline, glutamine, arginine, serine, threonine, valine, tryptophan and tyrosine. Tryptophan and methionine can oxidize relatively easily and in certain optional embodiments, are less preferred.

Methods for production of recombinant proteins with site specific incorporation of unnatural amino acids in host cells have been described in the literature, e.g., Liu et al., 2007, Nat. Methods 4(3):239-44, Xie et al., 2006 Nat. Rev. Mol. Cell. Biol. 7(10):775-82, Ryu et al., 2006, Nat. Methods 3(4): 263-65, Deiters et al., 2004, Bioorg. Med. Chem. Lett. 14(23): 5743-5, Bogosian et al., 1989, J. Biol. Chem. 264(1):531-9, Tang et al., 2002, Biochemistry 41(34):10635-45, Budisa et al., 1995, Eur. J. Biochem. 230(2): 788-96, and Randhawa et al., 1994, Biochemistry, 33(14):4352-62. Thus, the substitute amino acid can also include a modified or a less-typical amino acid such as: 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methylvaline, norvaline, norleucine and ornithine.

More preferred naturally-occurring amino acids optionally substituted for cysteine in recombinant ADA, include, e.g., alanine, serine, asparagine, glutamine, glycine, isoleucine, leucine, phenylalanine, threonine, tyrosine, and valine. Serine is most preferred, and is exemplified hereinbelow.

Accordingly, DNA molecules expressing wild-type human and bovine adenosine deaminase were obtained and subjected to codon optimization for expression in E. coli, and also mutated to express mutein rbADA and mutein rhADA each comprising a Ser residue at position 74 of the respective mature proteins (position 75 of the translated protein) in place of the naturally occurring Cys residue. These are $Ser_{74}$-rbADA (SEQ ID NO: 1) and $Ser_{74}$-rhADA (SEQ ID NO: 3), respectively. In addition, it should be noted that the natural bovine ADA as isolated from bovine intestine also has 6 residues posttranslationally removed from the C-terminal end. It is an optional feature of the present invention that the $Ser_{74}$-rbADA according to the invention is either expressed without the 6 C-terminal residues (as a mutein) or is post-translationally modified to remove the same C-terminal residues lacking in the purified natural bovine ADA.

It should be further noted that natural bovine ADA as isolated from bovine intestine has polymorphisms: with reference to SEQ ID NO: 5, bovine ADA polymorphisms include, e.g., glutamine at position 198 in place of lysine, alanine at position 245 in place of threonine; arginine at position 351 instead of glycine. It is therefore contemplated that recombinant position 74 mutein bovineADA according to the invention, can also have additional substitutions at one or more of the noted positions or analogs of those positions: Gln in place of $Lys_{198}$; Ala in place of $Thr_{245}$; Arg in place of $Gly_{351}$.

In a further aspect of the invention, the present invention provides isolated DNAs that encode mutein ADA having the amino sequence SEQ ID NO: 1 or SEQ ID NO:3 described herein. Other DNAs encoding the mutein ADA with one or more substitutions: Gln in place of $Lys_{198}$; Ala in place of $Thr_{245}$; Arg in place of $Gly_{351}$ are also contemplated with the scope of the invention.

A suitable expression vector can be prepared from genomic or cDNA encoding rhADA or rbADA, respectively, that is optionally under the control of a suitable operably connected inducible promoter. The DNA is preferably codon optimized for the appropriate host cell and mutated by any convenient art-known method, e.g., by high efficiency oligonucleotide-directed mutagenesis (Olsen D B and Eckstein F, Proc Natl Acad Sci USA 87: 1451-5; 1990), whole gene synthesis with overlapping long oligonucleotides (Vasantha N and Filpula D, Gene 76: 53-60; 1989), PCR mediated gene synthesis (Jayaraman K et al., Proc Natl Acad Sci USA 88: 4084-88; 1991), or overlap extension PCR (Pogulis R J et al., Methods Mol Biol 57: 167-76; 1996).

In general, prokaryotes are preferred for the initial cloning of DNA sequences and construction of the vectors useful in the invention. For example, *E. coli* K12 strain MM 294 (ATCC No. 31,446) is particularly useful. Other microbial strains, simply by way of example, that may be used include *E. coli* strains such as *E. coli* B and *E. coli* X1776 (ATCC No. 31,537). The aforementioned strains, as well as, e.g., *E. coli* strains W3110 (F-, lambda-, prototrophic, ATCC No. 27,325), K5772 (ATCC No. 53,635), and SR101, bacilli such as *Bacillus subtilis*, and other enterobacteriaceae such as *Salmonella typhimurium* or *Serratia marcesans*, and various pseudomonas species, may be used.

Generally, plasmid vectors containing replicon and control sequences that are derived from species compatible with the host cell are used in connection with these hosts. Conventional plasmid vectors are double-stranded circular DNA molecules preferably engineered with enzyme recognition sites suitable for inserting exogenous DNA sequences, an antibiotic selectable gene, an origin of replication for autonomous propagation in the host cell, and a gene for the discrimination or selection of clones that contain recombinant insert DNA. Available plasmid vectors suitable for use in *E. coli* include, for example, pET3, pET9, pET11 and the extended pET series (cataloged by Novagen Corporation), pBAD, trc, phoA, typ, and $O_{L/R}/P_{L/R}$ plasmids.

Simply by way of example, *E. coli* is typically transformed using pBR322, a plasmid derived from an *E. coli* species (see, e.g., Bolivar et al., 1977, *Gene*, 2: 95). pBR322 contains genes for ampicillin and tetracycline resistance and thus provides easy means for identifying transformed cells. Similarly, the pUC plasmids provide convenient cloning vectors with DNA molecules for selection and replication (Yanisch-Perron, et al., 1985, Gene 33:103-119, the disclosure of which is incorporated by reference herein in its entirety). The pBR322 plasmid, or other microbial plasmid or phage, must also contain, or be modified to contain, promoters that can be used by the microbial organism for expression of its own encoded proteins.

Those promoters most commonly used in recombinant DNA construction include the beta-lactamase (penicillinase) and lactose promoter systems (Chang et al., 1978 *Nature*, 375: 615; Itakura et al., 1977, *Science*, 198: 1056; Goeddel et al., 1979, *Nature*, 281: 544) and a tryptophan (trp) promoter system (Goeddel et al., 1980, *Nucleic Acids Res.*, 8: 4057; EPO Appl. Publ. No. 0036,776). While these are the most commonly used, other microbial promoters have been discovered and utilized, and details concerning their nucleotide sequences have been published, enabling a skilled worker to ligate them functionally with art known vectors, e.g., plasmid vectors.

Simply by way of example, transcriptional regulation in *E. coli* may be achieved with any of the following inducible promoters: lac, tap, phoA, araBAD, T7, trc, and derivatives of the lambda $P_L$ and $P_R$ promoters as well as others well known to the art (e.g., Makrides, 1996, Microbiol. Rev. 60:512-538, the disclosure of which is incorporated by reference herein in its entirety).

Suitable inducer conditions optionally compatible with the vector include, for example, arabinose, lactose, or heat induction, phosphate limitation, tryptophan limitation, to name but a few. Preferably, the inducer element is a Lac operon, which is inducible by isopropyl thiogalactoside ("IPTG").

A suitable signal sequence (signal peptide) may be derived from pelB, fd pIII, or ompA.

Suitable antibiotic selection markers are well known to the art and include, for example, those that confer ampicillin, kanamycin, chloramphenicol, rifampicin, or tetracycline resistance, among others.

Suitable origin of replication sequences include those found in the following plasmids: pUC19, pACYC177, pUB110, pE194, pAMB1, pIJ702, pBR322, pBR327, and pSC101.

Suitable termination sequences include, for example, phage fd major terminator, TΦ, and rrnB.

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. For expression in *Saccharomyces*, the plasmid YRp7, for example (Stinchcomb et al., 1979, Nature, 282: 39; Kingsman et al., 1979, Gene, 7: 141; Tschemper et al., 1980, Gene, 10: 157), is commonly used. This plasmid already contains the trp1 gene that provides a selection marker for a mutant strain of yeast lacking the ability to grow in tryptophan, for example, ATCC No. 44,076 or PEP4-1 (Jones, 1977, Genetics, 85: 12). The presence of the trp1 lesion as a characteristic of the yeast host cell genome then provides an effective environment for detecting transformation by growth in the absence of tryptophan.

The *Pichia pastoris* expression system has been shown to achieve high level production of several proteins (Cregg, J. M. et al., 1993, *Bio/Technology* 11: 905-910, the disclosure of which is incorporated by reference herein in its entirety) and may be employed to express ADA as a soluble protein in the cytoplasm of *Pichia pastoris*.

Suitable promoting sequences in yeast vectors include the promoters for 3-phosphoglycerate kinase (Hitzeman et al., J. 1980, Biol. Chem., 255: 2073) or other glycolytic enzymes (Hess et al., 1968, J. Adv. Enzyme Reg., 7: 149; Holland et al., 1978, Biochemistry, 17: 4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and transcription termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient. Other useful plasmid elements may include expressed genes encoding chaperone proteins, proline isomerase proteins, or disulfide shuffling proteins.

C. POLYMER CONJUGATES

In another aspect of the invention, the mutein ADA such as $Ser_{74}$-rbADA (SEQ ID NO: 1) and $Ser_{74}$-rhADA (SEQ ID NO: 3) protein is conjugated to a suitable polymer in order to make polymer conjugates.

In preferred aspects, the mutein ADA polypeptide is conjugated to a substantially non-antigenic polymer, preferably a polyalkylene oxide ("PAO").

The ADA-polymer conjugates generally correspond to formula (I):

$$[R-NH]_z-(ADA) \quad \quad (I)$$

wherein (ADA) represents the recombinant mutein adenosine deaminase or active fragment thereof;

NH— is an amino group of an amino acid found on the mutein ADA for attachment to the polymer;

(z) is a positive integer, preferably from about 1 to about 80, more preferably from about 5 to about 80, yet more preferably from about 11 to about 18; and R includes a substantially non-antigenic polymer residue that is attached to the ADA in a releasable or non-releasable form.

In more preferred aspects, the polymers include polyethylene glycol (PEG) wherein the PEG can be linear, branched or multi-armed PEG. Generally, polyethylene glycol has the formula:

$$-O-(CH_2CH_2O)_n-$$

wherein (n) is a positive integer, preferably from about 10 to about 2,300, more preferably from about 40 to about 2,300. The average molecular weight of the polymers ranges from about 2,000 to about 100,000 Da. More preferably, the polymers have an average molecular weight of from about 4,000 Da to about 45,000 Da, yet more preferably, 4,000 Da to about 20,000 Da. Most preferably, the PEG is about 5,000 Daltons. Other molecular weights are also contemplated so as to accommodate the needs of the artisan.

Alternatively, the polyethylene glycol (PEG) residue portion of the invention can be represented by the structure:

$$-Y_{11}-(CH_2CH_2O)_n-CH_2CH_2Y_{11}-,$$

$$-Y_{11}-(CH_2CH_2O)_n-CH_2C(=Y_{12})-Y_{11}-,$$

$$-Y_{11}-C(=Y_{12})-(CH_2)_{a11}-Y_{13}-(CH_2CH_2O)_n-$$
$$CH_2CH_2-Y_{13}-(CH_2)_{a11}-C(=Y_{12})-Y_{11}-,$$

$$-Y_{11}-(CR_{11}R_{12})_{a12}-Y_{13}-(CH_2)_{b11}-O-$$
$$(CH_2CH_2O)_n-(CH_2)_{b11}-Y_{13}-(CR_{11}R_{12})_{a12}-Y_{11}-,$$

$$-Y_{11}-(CH_2CH_2O)_n-CH_2CH_2-,$$

$$-Y_{11}-(CH_2CH_2O)_n-CH_2C(=Y_{12})-,$$

$$-C(=Y_{12})-(CH_2)_{a11}-Y_{13}-(CH_2CH_2O)_n-$$
$$CH_2CH_2-Y_{13}-(CH_2)_{a11}-C(=Y_{12})-, \text{ and}$$

$$-(CR_{11}R_{12})_{a12}-Y_{13}-(CH_2)_{b11}-O-(CH_2CH_2O)_n$$
$$-(CH_2)_{b11}-Y_{13}-(CR_{11}R_{12})_{a12}-,$$

wherein:

$Y_{11}$ and $Y_{13}$ are independently O, S, SO, $SO_2$, $NR_{13}$ or a bond;

$Y_{12}$ is O, S, or $NR_{14}$;

$R_{11-14}$ are independently selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy and substituted arylcarbonyloxy;

(a11), (a12), and (b11) are independently zero or a positive integer, preferably 0-6, and more preferably 0, 1, or 2; and (n) is an integer from about 10 to about 2300.

As an example, the PEG can be functionalized in the following non-limiting manner:

$$-C(=Y_{14})-(CH_2)_m-(CH_2CH_2O)_n-,$$

$$-C(=Y_{14})-Y-(CH_2)_m-(CH_2CH_2O)_n-,$$

$$-C(=Y_{14})-NR_{11}-(CH_2)_m-(CH_2CH_2O)_n-,$$

$$-CR_{15}R_{16}-(CH_2)_m-(CH_2CH_2O)_n-$$

wherein $R_{11}$, $R_{15}$, and $R_{16}$ are independently selected from among H, $C_{1-6}$ alkyls, aryls, substituted aryls, aralkyls, heteroalkyls, substituted heteroalkyls and substituted $C_{1-6}$ alkyls;

(m) is zero or is a positive integer, and preferably 1 or 2;

$Y_{14}$ is O or S; and (n) represents the degree of polymerization.

In these aspects, the polymer (R group) includes a capping group, i.e., a group which is found on the terminal of the polymer. The capping group can be selected from any of $NH_2$, OH, SH, $CO_2H$, $C_{1-6}$ alkyls, preferably methyl, as such groups are understood by those of ordinary skill.

In a further aspect, the polymer portion of the conjugate can be one which affords multiple points of attachment for the ADA. Alternatively, multiple PEGs can be attached to the ADA.

The pharmacokinetics and other properties of PEGylated ADA can be adjusted as needed for a desired clinical application by manipulation of the PEG molecular weight, linker chemistry and ratio of PEG chains to enzyme.

In these aspects, the ADA can be attached to the non-antigenic polymer in releasable or non-releasable form via various linkers known in the art.

The releasable polymer systems can be based on benzyl elimination or trimethyl lock lactonization. The activated polymer linkers of the releasable polymer systems can be prepared in accordance with commonly-assigned U.S. Pat. Nos. 6,180,095, 6,720,306, 5,965,119, 6,624,142 and 6,303,569, the contents of which are incorporated herein by reference. Alternatively, the ADA polymer conjugates are made using certain bicine polymer residues such as those described in commonly assigned U.S. Pat. Nos. 7,122,189 and 7,087,229 and U.S. patent application Ser. Nos. 10/557,522, 11/502,108, and 11/011,818, incorporated by reference herein. Other releasable polymer systems contemplated are also described in PCT/US07/78600, the contents of which are incorporated herein by reference.

Illustrative examples of releasable or non-releasable ADA polymer conjugates contemplated herein are described in U.S. Patent Application No. 60/913,039, the contents of which are incorporated herein by reference.

The polymer conjugation is preferably a PEGylation reaction as such reactions are known to those of ordinary skill. Briefly stated, mutein rbADA or rhADA, is reacted with an activated polymer to form ADA-polymer conjugates. In this regard, a wide variety of activated or functionalized polyethylene glycols can be used, including those described, for example in commonly assigned U.S. Pat. Nos. 5,122,614, 5,324,844, 5,612,460 and 5,808,096 (succinimidyl carbonate-activated polyethylene glycol (SC-PEG) and related activated PEG's), U.S. Pat. No. 5,349,001 (cyclic imide thione activated PEG's), U.S. Pat. No. 5,650,234, and others known to those of ordinary skill. The disclosure of each of the foregoing is incorporated herein by reference. See also activated polymers available from Nektar/Shearwater Polymers. Those of ordinary skill can use various activated fonts of the polymers for attachment without undue experimentation.

As will be appreciated by those of ordinary skill such conjugation reactions typically are carried out in a suitable buffer using a several-fold molar excess of activated PEG.

Some preferred conjugates made with linear PEGs like the above mentioned SC-PEG can contain, on average, from about 10 to about 80 PEG strands per ADA enzyme. Consequently, for these, molar excesses of several hundred fold, e.g., 200-1000× can be employed. The molar excess used for branched PEG and PEG attached to the enzyme will be lower and can be determined using the techniques described in the patents and patent applications describing the same that are mentioned herein.

In these aspects, the polyalkylene oxide is conjugated to the protein via linker chemistry including, e.g., succinimidyl carbonate, thiazolidine thione, urethane, and amide based linkers. The polyalkylene oxide is preferably covalently attached to an epsilon amino group of a Lys on the ADA, although other sites for covalent attachment are well known to the art. The ADA polymer conjugates can include at least 5 polyethylene glycol strands attached to epsilon amino groups of Lys on the enzyme, but alternatively, can include about 11-18 PEG strands attached to epsilon amino groups of Lys on the enzyme.

While the ADA is conjugated to from about 11 to about 18 PEG molecules per enzyme molecule, via lysine linkages, the ratio of PEG to ADA can be varied in order to modify the physical and kinetic properties of the combined conjugate to fit any particular clinical situation.

It will be apparent from the foregoing that additional aspects of the invention include using any commercially available or repotted activated PEG or similar polymer to conjugate the ADA enzyme or fragment thereof in order to provide conjugates useful for the methods of treatment described herein. See, e.g., the Nektar Advanced Pegylation catalog of 2004 (Nektar, San Carlos, Calif.), incorporated by reference herein in its entirety.

The activated PEGs can include linear, branched or U-PEG derivatives such as those described in U.S. Pat. Nos. 5,681,567, 5,756,593, 5,643,575, 5,919,455, 6,113,906, 6,566,506, 6,153,655, 6,395,266 and 6,638,499, 6,251,382 and 6,824,766 (also incorporated herein by reference). A non-limiting list of such polymers corresponds to polymer systems (i)-(vii) with the following structures:

(i)

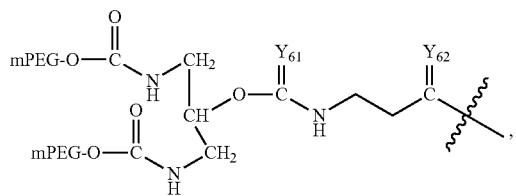

(ii)

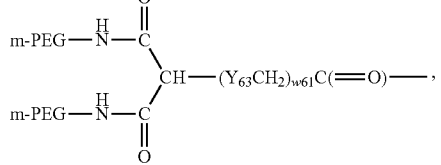

(iii)

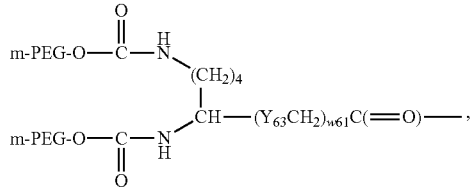

-continued (iv)

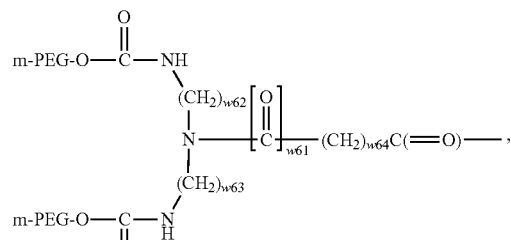

(v)

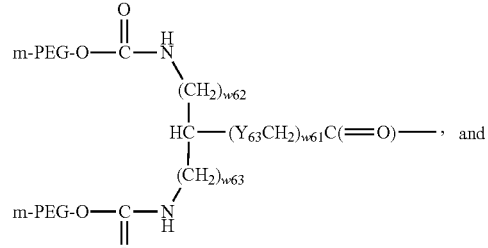

(vi)

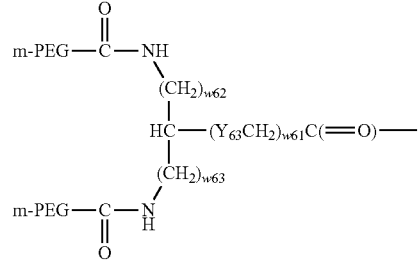

wherein:

$Y_{61-62}$ are independently O, S or $NR_{61}$;

$Y_{63}$ is O, $NR_{62}$, S, SO or $SO_2$ (w62), (w63) and (w64) are independently 0 or a positive integer, preferably from about 0 to about 10, more preferably from about 1 to about 6;

(w61) is 0 or 1;

mPEG is methoxy PEG wherein PEG is previously defined and a total molecular weight of the polymer portion is from about 2,000 to about 100,000 daltons; and $R_{61}$ and $R_{62}$ are independently the same moieties which can be used for $R_{11}$.

It will be further understood that in addition to the PEG-based polymers, a number of other polyalkylene oxides can also be used. For example, the conjugates of the present invention can be made by methods which include converting the multi-arm PEG-OH and "star-PEG" products such as those described in Shearwater Corporation's 2001 catalog "Polyethylene Glycol and Derivatives for Biomedical Application". See also NOF Corp. Drug Delivery System catalog, Ver. 8, April 2006. The disclosure of each of which is incorporated herein by reference. The multi-arm polymers contain four or more polymer arms and preferably four or eight polymer arms. For purposes of illustration and not limitation, the multi-arm polyethylene glycol (PEG) residue can be of the formula:

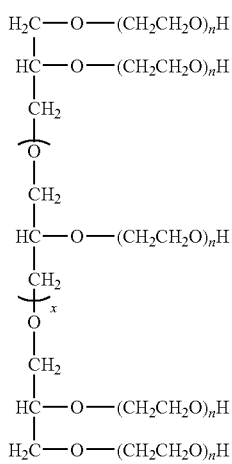

wherein:
(x) is 0 and a positive integer, i.e. from about 0 to about 28; and
(n) is the degree of polymerization.

In one particular embodiment of the present invention, the multi-arm PEG has the structure:

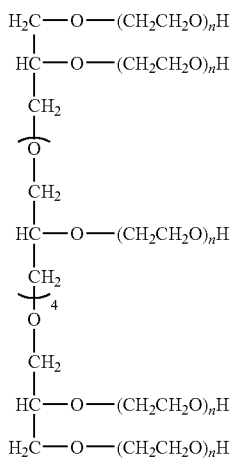

wherein (n) is a positive integer. In one preferred embodiment of the invention, the polymers have a total molecular weight of from about 2,000 Da to about 100,000 Da, and preferably from 4,000 Da to 45,000 Da.

In another particular embodiment, the multi-arm PEG has the structure:

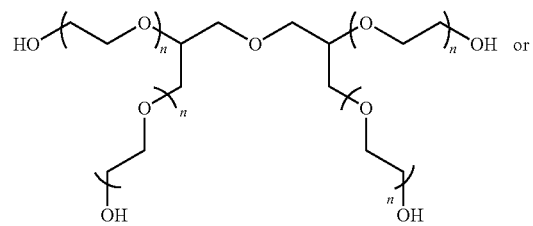 or

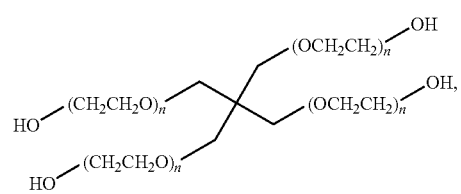

wherein n is a positive integer. In one preferred embodiment of the invention, the polymers have a total molecular weight of from about 2,000 Da to about 100,000 Da, and preferably from 4,000 Da to 45,000 Da.

The polymers can be converted into a suitably activated polymer, using the activation techniques described in U.S. Pat. No. 5,122,614 or 5,808,096. Specifically, such PEG can be of the formula:

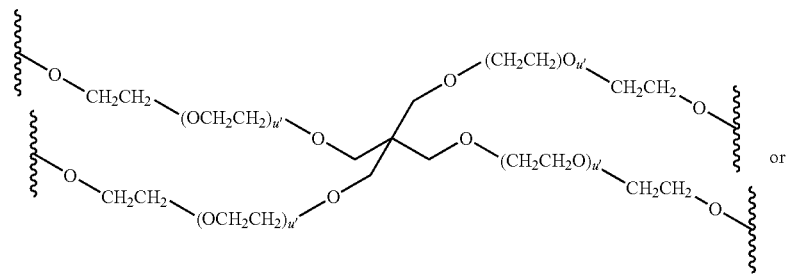

Star or

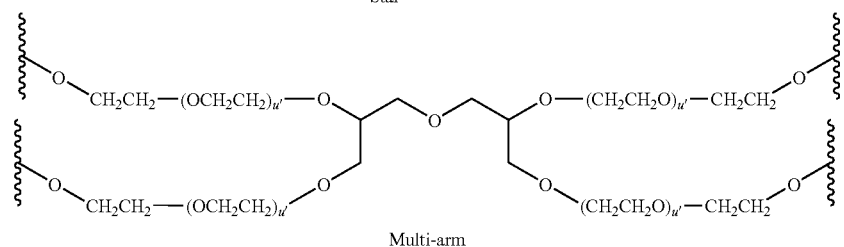

Multi-arm wherein:

(u') is an integer from about 10 to about 570, to preferably provide polymers having a total molecular weight of from about 2,000 Da to about 100,000 Da, and preferably, from about 4,000 Da to about 45,000 Da; and up to 3 terminal portions of the residue is/are capped with a methyl or other lower alkyl.

In some preferred embodiments, all 4 of the PEG arms are converted to suitable functional groups, i.e. SC, etc., for facilitating attachment to the recombinant protein. Such compounds prior to conversion include:

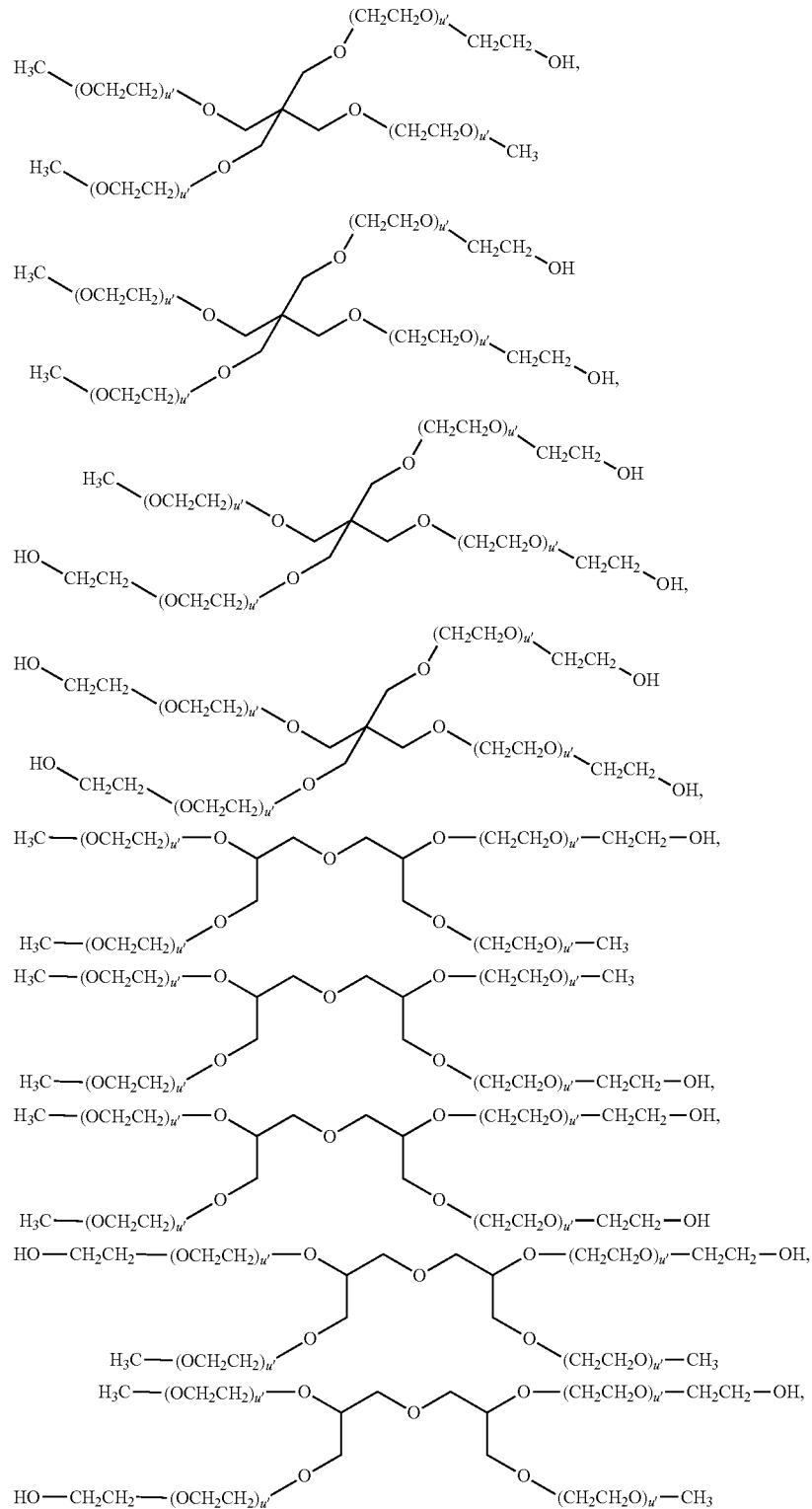

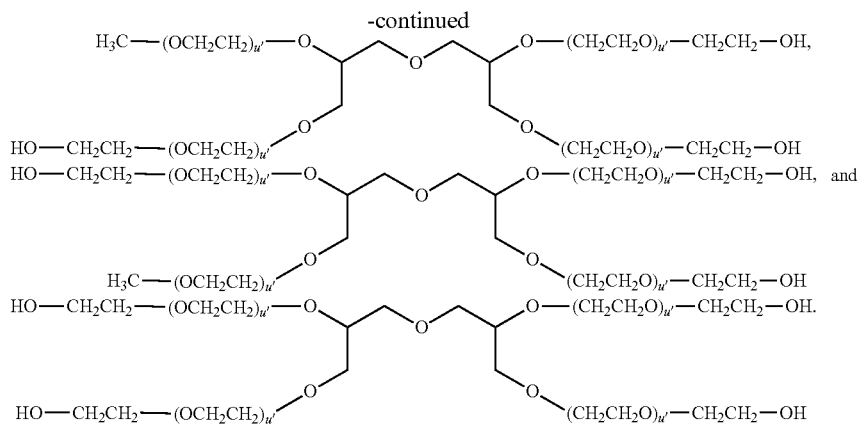

In most preferred aspects of the invention, the activated polyethylene glycol is one which provides a urethane linkage or amide-linkage with the protein.

In yet alternative aspects, the activated polymers can employ a hindered ester-based linker. See PCT/US07/78593 entitled "Polyalkylene Oxides Having Hindered Ester-Based Biodegradable Linkers", the content of which are incorporated by reference. For example, a non-limiting list of such compounds includes:

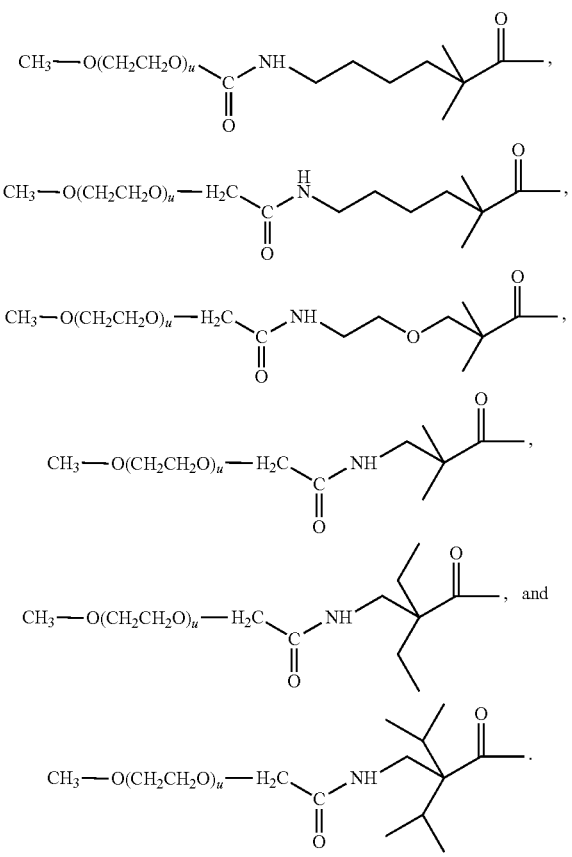

wherein (u) is an integer to preferably provide polymers having a total molecular weight of from about 2,000 Da to about 100,000 Da.

In one preferred embodiment, the PEG conjugate includes

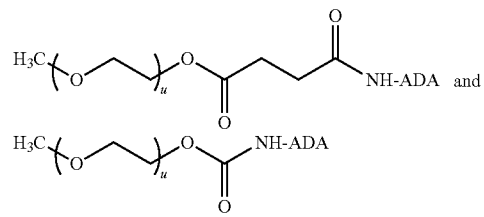

wherein (u) is an integer to provide the polymeric portion having a molecular weight of from about 2,000 Da to about 100,000 Da, and preferably from about 4,000 Da to about 45,000 Da, yet more preferably about 5,000 Da.

Suitable polymers will vary substantially by weight. Polymers having molecular number average weights ranging from about 2,000 to about 100,000 are usually selected for the purposes of the present invention. Molecular weights of from about 4,000 to about 45,000 are preferred and 5,000 to about 12,000 are particularly preferred. The polymeric substances included are also preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. In addition to mPEG, $C_{1-4}$ alkyl-terminated polymers are also useful.

Methods of preparing polymers having terminal carboxylic acids in high purity are described in U.S. patent application Ser. No. 11/328,662, the contents of which are incorporated herein by reference. The methods include first preparing a tertiary alkyl ester of a polyalkylene oxide followed by conversion to the carboxylic acid derivative thereof. The first step of the preparation of the PAO carboxylic acids of the process includes forming an intermediate such as t-butyl ester of polyalkylene oxide carboxylic acid. This intermediate is formed by reacting a PAO with a t-butyl haloacetate in the presence of a base such as potassium t-butoxide. Once the t-butyl ester intermediate has been formed, the carboxylic acid derivative of the polyalkylene oxide can be readily provided in purities exceeding 92%, preferably exceeding 97%, more preferably exceeding 99% and most preferably exceeding 99.5% purity.

In yet alternative aspects, polymers having terminal amine groups can be employed to make the ADA conjugates. The methods of preparing polymers containing terminal amines in high purity are described in U.S. patent application Ser. Nos. 11/508,507 and 11/537,172, the contents of each of which are incorporated by reference. For example, polymers having azides react with phosphine-based reducing agent such as t-phenylphosphine or an alkali metal borohydride reducing agent such as $NaBH_4$. Alternatively, polymers including leaving groups react with protected amine salts such as potassium salt of methyl-tert-butyl imidodicarbonate (KNMeBoc) or the potassium salt of di-tert-butyl imidodicarbonate (KN-$Boc_2$) followed by deprotecting the protected amine group. The purity of the polymers containing the terminal amines formed by these processes is greater than about 95% and preferably greater than 99%.

The branching afforded by the polymers of the U.S. Pat. No. 6,153,655, cited above, allows secondary or tertiary branching as a way of increasing polymer loading on a biologically active molecule from a single point of attachment. It will be understood that the water-soluble polymer can be functionalized for attachment to the bifunctional linkage groups if required without undue experimentation.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl pyrrolidones, polyacrylamides such as HPMA's (hydroxypropylmethacrylamides), polyvinyl alcohols, carbohydrate-based polymers, copolymers of the foregoing, and the like can be used. Those of ordinary skill in the art will realize that die foregoing list is merely illustrative and that all polymer materials having the qualities described herein are contemplated. For purposes of the present invention, "substantially or effectively non-antigenic" means all materials understood in the art as being nontoxic and not eliciting an appreciable immunogenic response in mammals.

D. UTILITY

The artisan will appreciate that the inventive mutein ADA is readily employed in a clinical setting for treating any disease or disorder responsive to ADA enzyme. Such a disease or disorder is one that responds to reduced tissue or blood levels of adenosine or deoxyadenosine. Such a disease or disorder can include, for example, SCID, pulmonary diseases, e.g., asthma, and cancers that respond to decreased local or systemic adenosine or deoxyadenosine levels. More detail on the use of ADA in treating tumors or cancers is provided by co-owned U.S. Ser. No. 12/105,682 filed on even date herewith (which claims the benefit of priority from U.S. Provisional patent Application Ser. No. 60/913,039), entitled: "Enzymatic Anticancer Therapy, and incorporated by reference herein in its entirety. The treating agent can be, for example, mutein rhADA or mutein rbADA enzyme. Preferably, the treating mutein rADA is polymer-conjugated, as described supra, e.g., PEGylated. The dosage of the ADA or polymer-conjugated ADA is individualized depending upon the clinical response of the tumor and the side effect profile of an individual patient, whether animal or human. In the example study provided herein below, the highest dose is the maximum feasible dose that is tolerated.

For example, Adagen® is commercially supplied as 250 U of bovine ADA/mL. This translates to 2000 U/kg for an approximate 25 g mouse injected with 0.2 ml of Adagen®. Of course, the artisan will appreciate that the dose of polymer-conjugated ADA can also be adjusted for the particular polymer size, linker chemistry, and valency. For example, the dosing regimen for a polymer conjugate comprising two or more ADA enzymes per polymer will be adjusted according to the units of ADA per ml of solution of any particular polymer conjugate of ADA.

In providing the ADA or ADA PEG-conjugate by injection, the optimal dose range is preferably set by plasma monitoring. It is generally desirable to provide the recipient with a dosage that will maintain plasma ADA activity (trough levels) in the range of from about 10 to 100 µmol/hr/mL, preferably from about 15 to about 35 µmol/hr/mL (assayed at 37° C.); and demonstrate a decline in erythrocyte adenosine, i.e., dATP to $\leq$about 0.001-0.057 µmol/mL, preferably about 0.005-about 0.015 µmol/mL in packed erythrocytes, or $\leq$about 1% of the total erythrocyte adenosine (i.e., ATP+ dATP content), with a normal adenosine level, as measured in a pre-injection sample. The normal value of dATP is below about 0.001 µmol/mL.

The dose based on the amount of enzyme will range from, for example, about 0.10 U/kg through about 30 U/kg, or higher, preferably from about 0.5 U/kg through about 20 U/kg, and more preferably from about 0.5 U/kg through about 12 U/kg (i.e. per kg of patient body weight) such as from about 0.5 U/kg through about 5 U/kg. A total weekly dose can be up to 40 U/kg, or more, as tolerated by the recipient. Further increases of 5 U/kg/week are permitted, up to a maximum single dose of 30 U/kg, or more, as tolerated by the recipient. In general, following weekly injections of ADAGEN® at 15 U/kg, the average trough level of ADA activity in plasma is between 20 and 25 µmol/hr/mL.

It should be noted that the dose of 100 U/kg is the mouse equivalent dose of approximately 12 U/kg clinical child dose.

Details of ADA dosage information are alt known as described in the prescription insert for ADAGEN® (Enzon, Inc.), the contents of which are incorporated herein.

EXAMPLES

The following examples serve to provide further appreciation of the invention but are not meant in any way to restrict the effective scope of the invention.

Example 1

Construction of *E. coli* Expression Strain Expressing Recombinant Human ADA with a Cys to Ser Chance at Position 74 of the Mature Protein The reported 363 amino acid sequence of human adenosine deaminase (GenBank NP_000013, incorporated by reference herein) was analyzed for the presence of cysteine codons. Five positions in the mature (N-terminal Met is cleaved) polypeptide encode cysteine (C74, C152, C153, C168, C261). In the designed and modified gene expressing human ADA, only one of these five cysteine codons (Cysteine 74, TGC) was changed to a serine codon (TCC) (this is position 75 in the translated protein). The defined polypeptide sequence (see SEQ ID NO: 3) was provided to Blue Heron Corporation (Bothell, Wash., U.S.A.) for whole gene synthesis of a new gene having codons optimized for expression in *E. coli*, using standard chemical synthesis of overlapping oligonucleotide segments. In brief, the sequence was optimized for bacterial expression by following the standard bacterial codon usage for *Escherichia coli* K12, using the codon data described by Grantham R. et al.; 1981, "Codon catalogue usage in genome strategy modulated for gene expressivity," *Nucleic Acid Res.* 9:r43-r47, and Lathe, R. 1985, "Synthetic oligonucleotide probes deduced from amino acid sequence data, Theoretical and practical considerations." *J. Mol Biol;* 183:1-12.

The corresponding RNA sequence was then analyzed for the formation of hairpin structure or loop formation and was subjected to minimum free energy calculations. The flanking restriction sites, NdeI and BamHI were included at the termini of the gene. Following digestion of the synthetic DNA with the restriction enzymes NdeI and BamHI, the 1.1 kilobase gene was ligated via T4 DNA ligase into the plasmid vector pET-28a (Novagen Corporation), which had also been digested with these two enzymes. The recombinant plasmid was introduced into *E. coli* strain BLR (DE3) or HMS174 (DE3) by electroporation using a BTX Electro Cell Manipulator 600 according to the manufacturer's instructions. The transformation mixture was plated on LB agar plates containing kanamycin (15 μg/ml) in order to allow for selection of colonies containing the plasmid pET-28a/ADAcysSer (designated ADAc75s/pET28a:BLR(DE3) or ADAc75s/pET28a:HMS174(DE3)). The ADA variant gene nucleotide sequence was verified by DNA sequence analysis with a ABI Prism 310 Genetic Analyzer using Big Dye Terminators. The DNA sequence encoding the $Ser_{74}$-rhADA open reading frame is according to SEQ ID NO: 4.

Isolated colonies were further purified by plating and analyzed for isopropyl β-D-1-thiogalactopyranoside ("IPTG") inducible gene expression in LB medium by standard methods such as those described in Novagen pET System Manual Ninth Edition, incorporated by reference herein.

Several induction parameters were examined including time, temperature and inducer concentration. A preferred condition was induction with 50 μM IPTG for 12 hrs at 25° C., which allowed high level production of ADA within die cytoplasm of the host bacteria at about 20% of total cell protein. The expressed ADA protein was confirmed on SDS PAGE analysis to exhibit the collect molecular weight of approximately 40 kDa (data not shown).

Example 2

Construction of *E. coli* Expression Strain Expressing Recombinant Bovine ADA with a Cys to Ser Change at Position 74 of the Mature Protein The purified mature ADA protein derived from bovine intestinal preparations is a 356 amino acid protein lacking the N-terminal methionine and also lacking the final six C-terminal residues predicted from the cDNA sequence (GenBank NP_776312, incorporated by reference herein). The bovine ADA amino acid sequence was analyzed for the presence of cysteine codons. Five positions in the mature polypeptide encode cysteine (C74, C152, C153, C168, C261). In the designed and modified bovine ADA synthetic gene, only one of these five cysteine positions (cysteine 74) was changed to a senile residue. This was performed by inserting a serine codon (TCC) in place of the normal cysteine codon at position 74 of the mature polypeptide (or position 75 of the translation product). The gene was also codon optimized for expression in *E. coli*.

In brief, the defined polypeptide sequence (see SEQ ID NO: 1) was provided to BioCatalytics Inc. for whole gene synthesis of a new gene having codons optimized for expression in *E. coli*, using their methods that include chemical synthesis of overlapping oligonucleotide segments. The BioCatalytics methods are described in greater detail by U.S. Pat. No. 6,366,860, the contents of which are incorporated by reference herein in their entirety.

Bovine ADA expression was investigated in several expression systems. For example, the flanking restriction sites, NdeI and BamHI were included at the termini of the gene. Following digestion of the synthetic DNA with the restriction enzymes NdeI and BamHI, the 1.1 kilobase gene was ligated via T4 DNA ligase into the plasmid vector pET-9d (Novagen Corporation), which had also been digested with these two enzymes. The recombinant plasmid was introduced into *E. coli* strain BLR (DE3) or HMS174 (DE3) by electroporation using a BTX Electro Cell Manipulator 600 according to the manufacturer's instructions. The transformation mixture was plated on LB agar plates containing kanamycin (15 μg/ml) to allow for selection of colonies containing the plasmid pET-9d/bADA (designated bADA/pET9d: BLR (DE3) or bADA/pET9d:HMS174(DE3)). The ADA variant gene nucleotide sequence was verified by DNA sequence analysis with a ABI Prism 310 Genetic Analyzer using Big Dye Terminators. The DNA molecule encoding the mutein ADA is shown by SEQ ID NO: 2.

Isolated colonies were further purified by plating and analyzed for IPTG inducible gene expression in LB medium by standard methods such as those described in Novagen pET System Manual Ninth Edition. Several induction parameters were examined including time, temperature and inducer concentration. A preferred condition was induction with 0.3% lactose for 12 hrs at 37° C., which allowed high level production of ADA within the cytoplasm of the host bacteria at about 20% of total cell protein. The ADA product was confirmed on SDS PAGE analysis to exhibit the collect molecular weight of approximately 40 kDa.

Example 3

Purification of Mutein rhADA Protein

The purification of mutein rhADA was carried out in a 3 chromatographic protocol developed by Enzon. Bacterial fermentation was conducted for *E. coli* expressing the rhADA protein from a synthetic gene on plasmid pET28a (Novagen) in host cell HMS174(DE3). Rifampicin (200 μg/ml) and kanamycin (30 μg/ml) were included in a minimal glycerol medium supplemented with yeast extract (30 g/l) and the cells were grown at 28° C. to an $OD_{600}$ of 11 when the inducer IPTG was added to 5 mM final concentration. After 40 hours ($OD_{600}$~110), the cells were harvested by centrifugation and frozen at −20° C. Briefly, thawed cell paste (50 g) was re-suspended in 1800 ml buffer of 10 mM Tris buffer [tris hydroxymethylaminomethane], 1 mM DTT, pH 8.0, and homogenized at 1200 RPM for 10 seconds with Tempest Virtis (Sentry™, Microprocessor, Boston, Mass.). This suspension was passed through a stainless steel mesh (Opening micrometer 250μ, No. 60, W. S Tyler) to remove big particles. The homogenous cell suspension was microfluidized for 3 cycles at 15,000 psi (unit was ice-bathed) (Micro Fluidizer, Microfluidics Corp., Model#110Y, Boston, Mass.). At the end of micro fluidization, 200 ml of the same buffer as above was used to rinse the unit and this solution was combined with the above suspension. The soluble protein from cell lysates was extracted by centrifugation at 16,000 rpm for 40 minutes at 4° C. (Sorvall® RC 5C plus, rotor SLA-1000). The supernatant was collected carefully to avoid unwanted mixing. The pH was adjusted to 8.0, and 1 mM $MgCl_2$ and 20 mg/mL DNase were added and incubated at room temperature for 2 hrs. The pH was then adjusted to 6.5 with 1 N HCl. A second centrifugation was conducted as above, the supernatant collected, and adjusted to 2 mM EDTA, followed by filtration on a Nalgene® 90 mm filter unit. The volume of the filtered supernatant was 500 ml, total protein concentration by BCA method was 8.5 mg/ml.

The cell extract (100 ml) was adjusted to pH 7.2, 4.5 mS/cm and loaded onto HiTrap® DEAE ff (ff" indicates "fast flow") at 20 mM Bis-Tris, 20 mM NaCl, pH 6.5 and eluted with 20 mM Bis-Tris, 500 mM NaCl, pH 6.5. The peak fractions were identified by enzyme assay and SDS-PAGE and adjusted to 1.5 M ammonium sulfate in 20 mM NaHPO$_4$, pH 6.5 and loaded onto a HiTrap Phenyl ff column. The protein was eluted with a gradient of load buffer and 20 mM NaHPO$_4$, pH 6.5. The peak fraction (55 ml; 0.4 mg/ml) was diafiltered against 20 mM NaHPO$_4$, 1 mM EDTA, 1 mM DTT, pH 6.5 and loaded onto HiTrap SP-Sepharose ff and eluted with 20 mM NaHPO$_4$, 500 mM NaCl, 1 mM EDTA, 1 mM DTT, pH 6.5. The collected fraction contained purified ADA protein (77 ml; 0.1 mg/ml).

Example 4

Purification of Recombinant Bovine ADA Protein

The purification of mutein rbADA expressed by the clone of Example 2 was carried out in a 3 chromatographic protocol developed by Enzon. Briefly, thawed cell paste (obtained from Blue Hereon or Biocatalytics, respectively) of 200 g which was stored at −80° C. was re-suspended in 1800 ml buffer of 20 mM Bis-Tris, 1 mM EDTA, pH 7.4, and homogenized at 1200 RPM for 5 min with Tempest Virtis (Sentry™, Microprocessor, Boston, Mass.). This suspension was passed through a stainless steel mesh (Opening micrometer 250µ, No. 60, W. S Tyler) to removed big particles. The homogenous cell suspension was microfluidized for 3 cycles at 15,000 psi (unit was ice-bathed) (Micro Fluidizer, Microfluidics Corp., Model# 110Y, Boston, Mass.). At the end of micro fluidization, 200 ml of the same buffer as above was used to rinse the unit and this solution was combined with the above suspension. The soluble protein from cell lysates was extracted by centrifugation at 7100 rpm (12000×g) for 60 minutes at 4° C. (Avanti J-201, Beckman Coulter; Rotor#JLA8.1000). The supernatant was collected carefully to avoid unwanted mixing.

To remove nucleotides in this cell extract, polyethyleneimine (PEI) was added to the above supernatant (final 0.15%, wt/v) and mixed thoroughly by stirring for 10 min. Then left this cell extract at 4° C. over night. The precipitant from this over night sample was removed by a centrifugation at 7100 rpm (12000×g), for 60 minutes at 4° C. (Avanti J-201, Beckman Coulter; Rotor# JLA8.1000). Similarly, the supernatant was collected carefully to avoid any unwanted mixing. To help ADA bind to the first column, 10% PEG4600 was added to this cell extract slowly and the pH of this cell extract was adjusted to 6.5 slowly with 1 N NaOH and 1N HCl. This supernatant was centrifuged again at 7100 rpm (12000×g), for 60 minutes at 4° C. (Avanti J-201, Beckman Coulter; Rotor# JLA8.1000) before loaded to the next column.

The cell extract was loaded to a pre-equilibrated Capto Q column (Cat#17-5316-01, GE Healthcare, Piscataway, N.J.). Bed volume 350 ml pre packed in a XK-50 column) with a buffer of 20 mM Bis-Tris, 1 mM EDTA, pH 6.5. Before ADA was eluted off from the column at 80 mM NaCl in the equilibration buffer, elutions at 60 mM and 70 mM NaCl were first performed to remove impurities. The elution profile was analyzed by ADA activity, SDS-PAGE analysis, Western Blots, and RP-HPLC.

After the Capto Q column, two hydrophobic interaction chromatographic ("HIC") purifications were used, one by one, to further polish the purity of the protein. The first HIC was Octyl Sepharose 4FF (Cat#17-0946-02, GE Healthcare, Piscataway, N.J.). The pool of ADA fractions from Capto Q column was adjusted to 1.5 M $(NH_4)_2SO_4$ with ammonium sulfate powder directly and the pH was adjusted to 6.5. The filtered sample (Nalgene Nunc, CAT #540887, MEMB 0.2 PES, Rochester, N.Y.) was loaded to the $1^{st}$ HIC column which was pre-equilibrated with 1.5 M $(NH_4)_2SO_4$, 20 mM potassium phosphate, 1 mM EDTA, pH 6.5 (Bed volume 150 ml, in XK-50, GE Healthcare, Piscataway, N.J.). The ADA protein was eluted with an ammonium sulfate gradient and the purity profile of this elution was determined by SDS-PAGE and RP-HPLC. The ADA protein in the fractions of first HIC column was pooled and adjusted to 1 M $(NH_4)_2SO_4$ and loaded directly to the second HIC column (Bed volume 150 ml, XK-50, HIC Phenyl HP, Cat#17-1082-01, Piscataway, N.J.) which was pre-equilibrated with 1 M $(NH_4)_2SO_4$, 20 mM $KH_2PO_4$—$K_2HPO_4$, 1 mM EDTA, pH 6.5. ADA was eluted with an ammonium sulfate gradient from 1 M to 300 mM in the 20 mM $KH_2PO_4$—$K_2HPO_4$, 1 mM EDTA, pH 6.5. ADA purity of these fractions was analyzed by SDS-PAGE and RP-HPLC. The purified rbADA or rhADA was further desalted and concentrated in a LabScale™ TFF systems (Membrane BioMax 5. Bedford, Mass.) against the storage buffer (for example, 100 mM sodium phosphate, 1 mM EDTA, pH 6.5).

Example 5

Stability Studies on rbADA and Scr74-rbADA

The following studies were done to demonstrate that the stability of rhADA towards oxidative degradation was indeed improved by mutating cys74 to ser. Samples of recombinant bovine ADA (rbADA) and recombinant bovine ADA mutated from cys74 to ser74 ($Ser_{74}$-rbADA) at concentrations of approximately 0.5 mg/mL in sodium phosphate buffer (pH 7.8) were used for the stability study. Stability was monitored by reversed-phase HPLC (RP-HPLC) using both UV detection at 220 nm and mass spectrometric detection (Micromass Q-TOF electrospray mass spectrometer). The HPLC conditions were as follows:
Column: Zorbax 300 SB-C8 (Agilent, 250×4.6 mm, 300 angstrom pore size, 5 micron particle size).
Mobile Phase A: 0.1% trifluoroacetic acid in water.
Mobile Phase B: 0.1% trifluoroacetic acid in acetonitrile/water (80/20; v/v).

| Gradient: | |
|---|---|
| Time | % Mobile Phase B |
| 0 | 20 |
| 5 | 20 |
| 45 | 80 |
| 46 | 20 |
| 60 | 20 |

Column temperature: 40° C.
Flow rate: 1.0 mL/min.
Injection volume: 50 µL.
Purity of the compounds was determined by RP-HPLC analysis at the initial time the stability study was started and at various timepoints, including 4, 8, and 17 days, after initiation of the study. It should be noted that the rbADA (non-mutein) samples were approximately two months old at the stair of this study and had already suffered some degradation. The Ser$_{74}$-rbADA sample had been freshly prepared and was relatively pure. However, for the purpose of the present study, the difference in purity between the initial time point and after 17 days incubation at 25° C. is the relevant parameter to examine.

As shown in Table 1, the purity of rbADA was 83.7% at the initial time point and decreased to 66.1% after 17 days, indicating that 17.6% of rbADA has degraded over this time period. Mass spectrometric analysis of the peaks separated chromatographically indicated that the major degradant eluting at 31.851 min, accounting for 30.5% of the area of the chromatogram, had a mass 32 Da higher than that of rbADA. This mass change is consistent with the addition of 2 oxygens to rbADA to form the sulfinic acid degradant of the free cysteine at position 74 of rbADA. The smaller degradant peak, eluting at 32.538 min, had a mass consistent with die addition of 1 oxygen to rbADA to form the sulfenic acid degradant of the free cysteine at position 74 of rbADA. Ser$_{74}$-rbADA, having a serine residue replacing the reactive cysteine74 residue, shows little degradation over the course of 17 days, with purities virtually the same at the initial time point (97.2%) and 17 days later (97.9%). This proves that cysteine74 is indeed the source of the oxidative degradation that occurs in rbADA and mutation of this residue to serine, which is not susceptible to oxidation, eliminates the degradation.

TABLE 1

Stability of rbADA, and Ser$_{74}$-rbADA in sodium phosphate buffer (pH 7.8) at 25° C.

| Time point | % Purity as Determined by RP-HPLC | |
| --- | --- | --- |
| | rbADA | Mut-rbADA |
| Initial | 83.7 | 97.2 |
| 4 Days | 83.6 | 96.7 |
| 8 Days | 76.3 | 97.7 |
| 17 Days | 66.1 | 97.9 |

Example 6

Use of Mutein ADA Proteins in Therapy of ADA-Deficient SCID Patients

The described mutated ADA enzymes are utilized in therapeutic settings that now employ ADAGEN. The Ser$_{74}$-rb or rhADA may be modified by conjugation with polyethylene glycol (PEG) with, for example, 11-17 PEG 5 kDa polymers per ADA protein. PEGylated preparations of mutein ADA are formulated in sterile saline solution at pH 7.2-7.4 and at a concentration of about 250 units per milliliter. The PEGylated mutein ADA is administered to patients by parenteral administration, such as by intramuscular administration. Patients benefiting from such therapy include those with severe combined immunodeficiency disease caused by insufficient ADA activity. Administration of the mutein PEG-ADA is typically every seven days with a dosing schedule of 10 U/kg for the first dose and 20 U/kg per week for maintenance doses. The Ser$_{74}$-rb or rh PEG-ADA is stored at 2-8° C. in aqueous solution with only one dose per 1.5 milliliter vial. The dosing schedule is designed to maintain plasma ADA activity levels at 15-35 µmol/hr/mL (assayed at 37° C.) and reduce erythrocyte dATP to $\leq$0.005-0.015 µmol/mL packed erythrocytes.

Example 7

Preparation of PEGylated Ser$_{74}$-rbADA Via Urethane Linkage

SC-PEG (N-hydroxysuccinimidyl carbonate-activated polyethylene glycol, 0.084 mmol) is added to a solution of Ser$_{74}$-rbADA (0.00027 mmol) in 3 mL of sodium phosphate buffer (0.1 M, pH 7.8) with gentle stirring. The solution is stilled at 30° C. for 30 minutes. A GPC column (Zorbax GF-450) is used to monitor PEG conjugation. At the end of the reaction (as evidenced by the absence of native enzyme), the mixture is diluted with 12 mL of formulation buffer (0.05 M sodium phosphate, 0.85% sodium chloride, pH 7.3) and diafiltered with a Centriprep concentrator (Amicon) to remove the unreacted PEG. Dialfiltration is continued as needed at 4° C. until no more free PEG is detected by mixing equal amount of filtrate and 0.1% PMA (polymethacrylic acid in 0.1 M HCl).

Example 8

Preparation of PEGylated Ser$_{74}$-rhADA Via Urethane Linkage

SC-PEG (0.084 mmol) is reacted with Ser$_{74}$-rhADA (0.00027 mmol) using the same conditions as described in Example 7.

Example 9

Preparation of PEGylated Ser$_{74}$-rbADA Via Amide Linkage

SS-PEG (N-hydroxysuccinimidyl succinate-activated polyethylene glycol, 0.084 mmol) is added to a solution of Ser$_{74}$-rbADA (0.00027 mmol) in 3 mL of sodium phosphate buffer (0.1 M, pH 7.8) with gentle stirring. The solution is stirred at 30° C. for 30 minutes. A GPC column (Zorbax GF-450) is used to monitor PEG conjugation. At the end of the reaction (as evidenced by the absence of native enzyme), the mixture is diluted with 12 mL of formulation buffer (0.05 M sodium phosphate, 0.85% sodium chloride, pH 7.3) and diafiltered with a Centriprep concentrator (Amicon) to remove the unreacted PEG. Dialfiltration is continued as needed at 4° C. until no more free PEG is detected by mixing equal amount of filtrate and 0.1% PMA (polymethacrylic acid in 0.1 M HCl).

Example 10

Preparation of PEGylated Mutein rhADA Via Amide Linkage

SS-PEG (0.084 mmol) is reacted with mutein rhADA (0.00027 mmol) using the same conditions as described in Example 9.

We claim:

1. An isolated recombinant adenosine deaminase comprising the polypeptide of SEQ ID NO:1, or an isolated recombinant adenosine deaminase variant polypeptide of SEQ ID NO:1, wherein the polypeptide variant of SEQ ID NO:1 comprises one or more amino acid substitutions selected from the group consisting of: Gln in place of $Lys_{198}$; Ala in place of $Thr_{245}$; and Arg in place of $Gly_{351}$.

2. The recombinant adenosine deaminase of claim 1 that is encoded by the DNA molecule of SEQ ID NO: 2.

3. A polyalkylene oxide-adenosine deaminase conjugate, wherein the adenosine deaminase is the recombinant adenosine deaminase of claim 1.

4. The polyalkylene oxide-adenosine deaminase conjugate of claim 3, wherein the polyalkylene oxide is polyethylene glycol.

5. The polyalkylene oxide-deaminase conjugate of claim 4, wherein the polyethylene glycol is conjugated to the recombinant adenosine deaminase via a linker selected from the group consisting of succinimidyl carbonate, thiazolidine thione, urethane, and amide base linkers.

6. The polyalkylene oxide-adenosine deaminase conjugate of claim 4, wherein the polyethylene glycol is covalently attached to an epsilon amino group of a Lys of the recombinant adenosine deaminase.

7. The polyalkylene oxide-deaminase conjugate of claim 4, wherein the recombinant adenosine deaminase comprises one or more polyethylene glycol strands attached to epsilon amino groups of one or more Lys residues of the recombinant adenosine deaminase.

8. The polyalkylene oxide-deaminase conjugate of claim 4, wherein the recombinant adenosine deaminase comprises from about 11 to about 18 polyethylene glycol strands attached to epsilon amino groups of one or more Lys residues of the recombinant adenosine deaminase.

9. The polyalkylene oxide-adenosine deaminase conjugate of claim 4, wherein the polyalkylene glycol is conjugated to the recombinant adenosine deaminase via a succinimidyl carbonate linker.

10. The polyalkylene oxide-adenosine deaminase conjugate of claim 4, wherein the polyethylene glycol has a molecular weight of from about 2,000 to about 100,000.

11. The polyalkylene oxide-adenosine deaminase conjugate of claim 4, wherein the polyethylene glycol has a molecular weight of from about 4,000 to about 45,000.

12. A method of treating an adenosine-deaminase-mediated condition in a mammal, wherein the condition is severe combined immunodeficiency disorder, comprising administering to the mammal a composition comprising a therapeutically effective amount of the recombinant adenosine deaminase of claim 1.

13. A process for purifying the recombinant adenosine deaminase of claim 1, comprising purifying the protein by ion exchange chromatography.

14. A process for purifying the recombinant adenosine deaminase of claim 1, comprising purifying the protein by hydrophobic interaction chromatography.

15. A recombinant adenosine deaminase produced by the process claim 13.

16. A recombinant adenosine deaminase produced by the process of claim 14.

17. An isolated DNA that encodes a recombinant adenosine deaminase having the amino acid sequence comprising SEQ ID NO: 1.

18. An isolated DNA that encodes the recombinant adenosine deaminase of claim 1.

19. The isolated recombinant adenosine deaminase of claim 1 comprising the polypeptide of SEQ ID NO: 1.

\* \* \* \* \*

UNITED STATES PATENT AND TRADEMARK OFFICE
CERTIFICATE OF CORRECTION

| | | |
|---|---|---|
| PATENT NO. | : 8,071,741 B2 | Page 1 of 1 |
| APPLICATION NO. | : 12/105913 | |
| DATED | : December 6, 2011 | |
| INVENTOR(S) | : David R. Filpula et al. | |

It is certified that error appears in the above-identified patent and that said Letters Patent is hereby corrected as shown below:

Col. 39, line 21 in claim 1,
"Gin" should read --Gln--.

Signed and Sealed this
Twenty-seventh Day of March, 2012

David J. Kappos
*Director of the United States Patent and Trademark Office*